United States Patent
Netoff et al.

(10) Patent No.: US 10,071,248 B2
(45) Date of Patent: Sep. 11, 2018

(54) SYSTEMS AND METHODS FOR TUNING CLOSED-LOOP PHASIC BURST STIMULATION BASED ON A PHASE RESPONSE CURVE

(71) Applicant: REGENTS OF THE UNIVERSITY OF MINNESOTA, St. Paul, MN (US)

(72) Inventors: Theoden Netoff, Minneapolis, MN (US); Dan Wilson, Santa Barbara, CA (US); Jeff Moehlis, Santa Barbara, CA (US); Abbey Holt Becker, Minneapolis, MN (US)

(73) Assignees: Regents of the University of Minnesota, St. Paul, MN (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/344,723

(22) Filed: Nov. 7, 2016

(65) Prior Publication Data
US 2017/0128729 A1     May 11, 2017

Related U.S. Application Data

(60) Provisional application No. 62/252,192, filed on Nov. 6, 2015.

(51) Int. Cl.
*A61N 1/36*     (2006.01)
*A61N 1/05*     (2006.01)

(52) U.S. Cl.
CPC ....... *A61N 1/36139* (2013.01); *A61N 1/0534* (2013.01); *A61N 1/36067* (2013.01); *A61N 1/36178* (2013.01)

(58) Field of Classification Search
None
See application file for complete search history.

(56) References Cited

U.S. PATENT DOCUMENTS

| | | | |
|---|---|---|---|
| 9,814,885 B2* | 11/2017 | Molnar | A61N 1/36185 |
| 2011/0230936 A1* | 9/2011 | Jensen | A61N 1/36067 607/62 |
| 2012/0071947 A1* | 3/2012 | Gupta | A61N 1/36139 607/45 |
| 2014/0236257 A1* | 8/2014 | Parker | A61B 5/04001 607/46 |
| 2014/0243714 A1* | 8/2014 | Ward | A61B 5/04 601/2 |

* cited by examiner

*Primary Examiner* — Kennedy Schaetzle
(74) *Attorney, Agent, or Firm* — Quarles & Brady LLP

(57) ABSTRACT

Systems and methods are provided for determining optimized settings for a closed-loop stimulation system based on analyzing a phase response curve measured from electrophysiological activity, such as electrical nerve activity or electrical muscle activity. The slope of the phase response curve is computed and used to determine a phase window during which phasic burst stimulation should be provided to achieve a desired effect on oscillations in the subject. When the slope of the phase response curve is positive, a phasic burst stimulation applied during the phase window will decrease synchrony of the oscillations. When the slope of the phase response curve is negative, a phasic burst stimulation applied during the phase window will increase synchrony of the oscillations.

19 Claims, 16 Drawing Sheets

SYSTEMS AND METHODS FOR TUNING CLOSED-LOOP PHASIC BURST STIMULATION BASED ON A PHASE RESPONSE CURVE

CROSS-REFERENCE TO RELATED APPLICATIONS

This application is related to, and incorporates herein by reference in its entirety, U.S. Application Ser. No. 62/252,192, filed Nov. 6, 2015, and entitled "Systems and Methods for Tuning Closed-Loop Phasic Burst Stimulation Based on a Phase Response Curve."

STATEMENT REGARDING FEDERALLY SPONSORED RESEARCH

This invention was made with government support under 1264432 awarded by the National Science Foundation. The government has certain rights in the invention.

FIELD OF THE INVENTION

This document relates generally to closed-loop stimulation, such as closed-loop deep brain stimulation, and more particularly to systems and methods for identifying optimized settings for delivering electrical stimulations based on phase response curves.

BACKGROUND OF THE INVENTION

Deep brain stimulation ("DBS") is a neuromodulation therapy effective at treating a range of neurological symptoms and conditions, including motor symptoms of patients with medication-refractory Parkinson's disease ("PD"). Tuning stimulation parameters is currently done using a time intensive trial-and-error process. For example, with DBS for treatment of motor symptoms of PD patients, high frequency stimulation (greater than 100 Hz) is conventionally tuned for each patient using a trial-and-error process. Some implantable DBS devices can simultaneously deliver stimulation while recording the neural response. As yet, these devices do not effectively use a closed-loop approach to setting stimulation parameters.

Dynamic changes in the basal ganglia network are thought to lead to motor symptoms of PD. A loss of dopaminergic inputs results in changes in firing rates and patterns of neurons within the basal ganglia. The emergence of synchronous activity, particularly in the beta range (12-35 Hz), is associated with motor symptoms in PD. Therapeutic DBS is effective at disrupting the pathological oscillation, making the beta oscillation a possible biomarker for closed-loop stimulation. Phasic stimulation may provide a closed-loop approach to disrupting this pathological beta oscillation, as stimulation at specific phases of an oscillation can either disrupt or enhance the oscillation. The frequency of stimulation affects therapeutic outcome in DBS for PD (e.g., frequencies greater than 100 Hz are therapeutic). This may be because stimulation at certain frequencies results in more stimulus pulses occurring at the optimal phase for desynchronization than at other frequencies.

There remains a need, however, to provide systems and methods that are capable of determining optimized settings for delivering electrical stimulations using a closed-loop stimulation system.

SUMMARY OF THE INVENTION

The present invention overcomes the aforementioned drawbacks by providing for more effective closed-loop control of stimulation systems. By measuring electrophysiological activity signals from a subject, a phase response curve ("PRC") can be estimated, and a slope of the PRC computed. Electrical stimulation parameters can be based on the computed slope of the PRC. The closed-loop stimulation system can then be controlled to apply stimulation according to the stimulation parameters.

Exemplary embodiments provide a closed-loop approach to tuning deep brain stimulation ("DBS") systems for Parkinson's disease ("PD") patients. The approach uses phasic burst stimulation ("PhaBS"), applying a burst of stimulus pulses over a range of phases predicted to disrupt pathological oscillations seen in PD. Stimulation parameters are optimized based on PRCs measured from each patient. Optimizing the stimulus phase using the PRC can make the PhaBS more effective at suppressing the pathological oscillation than a single phasic stimulus pulse. PhaBS provides a closed-loop approach to DBS that can be optimized for each individual patient.

The disclosed systematic approach to tuning stimulation parameters based on patient physiology has the potential to greatly improve patient quality of life. A closed-loop tuning algorithm can reduce time in the clinic for setting stimulation parameters, and provide more robust and effective tuning. Moreover, a closed-loop device can continuously tune parameters to maintain maximal efficacy as motor symptoms fluctuate. A closed-loop approach to DBS with PhaBS, for example, allows the timing of stimulus pulses to be optimized using algorithms based on patient physiology. Such a closed-loop approach has the potential to improve therapeutic efficacy, extend battery lifetime by decreasing power consumption, decrease negative side effects by stimulating more selectively, and make adjustments as symptoms fluctuate.

The foregoing and other aspects and advantages of the invention will appear from the following description. In the description, reference is made to the accompanying drawings that form a part hereof, and in which there are shown by way of illustration of preferred embodiments of the invention. Such embodiments do not represent the full scope of the invention, however, and reference is made therefore to the claims herein for interpreting the scope of the invention.

DETAILED DESCRIPTION OF THE INVENTION

Figure 1:
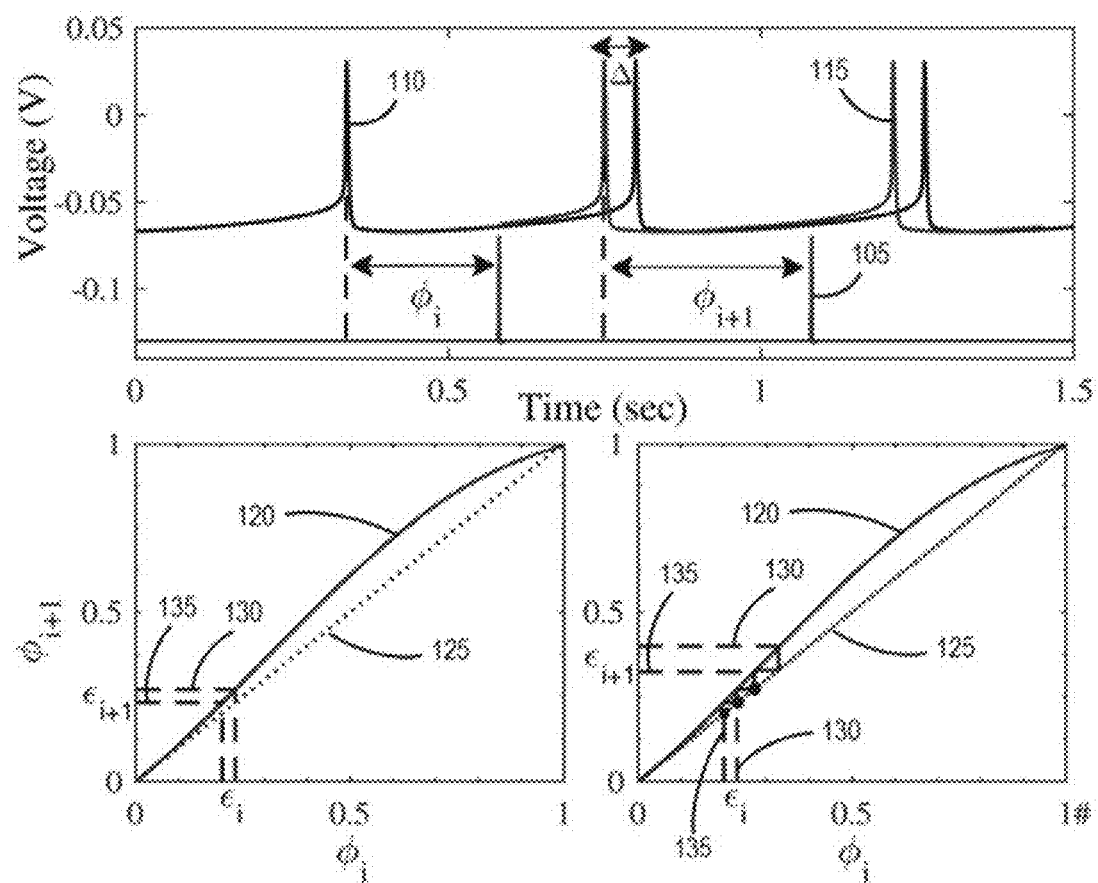
FIG. 1 illustrates that phase response curves can be used to predict synchronization properties of a periodic stimulus. Top: Current pulses for a periodic stimulus (pulses 105) can be applied to a periodically firing neuron (black trace 110). The stimulus pulse is applied at a specific phase ($\phi_i$) in the cycle of the neuron. This results in a change in the timing of the next action potential (voltage trace 115). The difference in spike timing is measured as the spike time advance ($\Delta \phi_i$). The stimulus will now fall at a different phase ($\phi_{i+1}$) on the next cycle. Bottom left: The phase of the stimulus on the next cycle can be predicted from the PRC map (120; PRC added to the black dotted line of identity 125). Given the phase of the current stimulus pulse ($\phi_i$), the map can be used to predict the phase on the next cycle ($\phi_{i+1}$). The slope of the PRC map at the stimulus phase affects how two neurons (dashed lines 130, 135) will synchronize or desynchronize. Here, where the slope of the PRC map is greater than the diagonal (i.e., greater than 1), the two neurons (130, 135) starting at some small distance in phase apart ($\epsilon_i$) are further apart on the next cycle, $\epsilon_{i+1} > \epsilon_i$. Bottom right: The PRC map can be used to predict the stimulus phase on the next cycle ($\phi_{i+1}$) for a burst of three stimulus pulses. Here each stimulus pulse is applied at a phase where the slope of the PRC map is positive. This results in a greater separation of the two neurons on the next cycle ($\varepsilon_{i+1}$) than when a single pulse was used (bottom left).

Described here are systems and methods for determining optimized settings for a closed-loop stimulation system based on analyzing a phase response curve measured from electrophysiological activity, such as electrical nerve activity or electrical muscle activity. As one example, the closed-loop stimulation system can include a deep brain stimulation system. In other examples, however, the closed-loop stimulation system can include other nerve stimulation devices, such as those that provide electrical stimulation to other regions of the central nervous system or to the peripheral nervous system. The closed-loop stimulation system can also provide electrical stimulation to muscles, including cardiac muscle, skeletal muscle, and smooth muscle.

As one non-limiting example, evidence obtained from open-loop stimulation in patients with PD and essential tremor finds that phasic stimulation modulates the pathological oscillation amplitude. While efficacy of phasic stimulation was significant in previous studies, effects were small. There are two reasons why a stronger effect may not have been seen. First, extended periods of phasic stimulation may be required, which is not possible with open-loop stimulation. Second, a single stimulus pulse per cycle may not be optimal for suppressing the oscillation.

Phasic burst stimulation is a closed-loop approach that applies a burst of stimulus pulses over a range of phases. An algorithm is used to optimize the stimulus phase onset as well as the burst frequency to maximally suppress pathological oscillations. While many of the examples described here focus on designing stimulations to suppress pathological beta oscillations, the methods described here can be readily implemented to suppress or enhance any population oscillation.

In order to identify the phase window over which stimulation will optimally increase or decrease neuronal synchrony, a phase response curve ("PRC") can be estimated and analyzed. A PRC is a measure of how the phase of a perturbation, such as an external stimulus, affects the phase of an oscillation, and can be used to predict when coupled oscillators, such as periodically firing neurons, will synchronize or desynchronize.

To determine optimized settings for a closed-loop stimulation system, exemplary embodiments of the present invention implement an analysis of a phase response curve to predict how phasic stimulation locked to an oscillation will achieve a desired effect, such as desynchronizing neurons. The phase advance, $\Delta$, that occurs from a stimulus applied at phase, $\phi$, is characterized by a function, $Z(\phi)$, which can be measured directly from electrophysiological activity, such as from a neuron or population of neurons. The function, $Z(\phi)$, is referred to as the phase response curve ("PRC"). When stimulation of an oscillator is periodic, the PRC can be used to predict the phase of the stimulus on the next cycle, $\phi_{i+1}$, from the phase on the current cycle, $\phi_i$, via a map, $$\phi_{i+1} = \phi_i + Z(\phi_i) \tag{1}$$

Using neuronal activity as an example, two neurons that are nearly synchronized (i.e., separated in phase by $\epsilon$) will be farther apart after a stimulus if the slope of the map at the phase of the stimulus is greater than one, $$\delta_{i+1} = \epsilon_i (1 + Z'(\phi_i)) \tag{2}$$

as shown in FIG. 1, which illustrates how phase response curves can be used to predict synchronization properties of a periodic stimulus. Application of the stimulus over several cycles at desynchronizing phases will cause the neurons' phase to diverge and desynchronize. The optimal stimulus phase to desynchronize the neurons for a single pulse per cycle of the oscillation is the phase at which the map has the steepest positive slope. However, a burst of stimulation applied over the entire phase range where the slope of the map is greater than one will desynchronize the neurons faster than a single pulse.

In the top panel of FIG. 1, current pulses for a periodic stimulus (pulses 105) can be applied to a periodically firing neuron (trace 110). The stimulus pulse is applied at a specific phase, $\phi_i$, in the cycle of the neuron. This results in a change in the timing of the next action potential (voltage trace 115). The difference in spike timing is measured as the spike time advance, $\phi_i$. The stimulus will now fall at a different phase, $\phi_{i+1}$, on the next cycle.

In the bottom left panel of FIG. 1, it is illustrated that the phase of the stimulus on the next cycle can be predicted from the PRC map. Given the phase of the current stimulus pulse, $\phi_i$, the PRC map can be used to predict the phase on the next cycle, $\phi_{i+1}$. The slope of the PRC map at the stimulus phase affects how two neurons will synchronize or desynchronize. Here, where the slope of the PRC is greater than one, the two neurons starting at some small distance in phase apart, $\epsilon_i$, are farther apart on the next cycle, $\epsilon_{i+1}$. In the bottom right panel of FIG. 1, it is illustrated that the PRC map can be used to predict the stimulus phase on the next cycle, $\phi_{i+1}$, for a burst of three stimulus pulses. Here, each stimulus pulse is applied at a phase where the slope of the PRC map is positive, which results in a greater separation of the two neurons on the next cycle, $\epsilon_{i+1}$, than when a single pulse was used (e.g., in the bottom left panel of FIG. 1).

PRC theory can be described using two periodically firing neurons starting relatively close together in phase. The distance in phase between the two neurons on the next cycle can be determined from the PRC and their distance, $\epsilon$, on the current cycle $\epsilon_{i+1} = \epsilon_i \times (1 + Z'(\phi_i))$. If the absolute value of the slope of the map at the phase the stimulus is delivered is greater than one, then the distance between the neurons will grow, as shown in FIG. 1. Application of the stimulus over several cycles at these phases will cause the neurons' phases to diverge and desynchronize. The optimal stimulus phase to desynchronize the neurons with a single pulse per cycle of the oscillation is the phase at which the map has the steepest positive slope. In this description, the oscillators are individual neurons. However, in the Hahn & McIntyre model (further discussed below), there is a population oscillation, where the populations of neurons are the oscillators. A burst of stimulation pulses applied over a range of phases where the absolute value of the slope of the map is greater than one will increase the phase difference between the neurons on the next cycle over a single pulse. Assuming no interaction between stimuli, this is shown in FIG. 1. Burst stimulation is expected to be more effective at desynchronizing a population of neurons than pulsatile stimulation.

Figure 2:
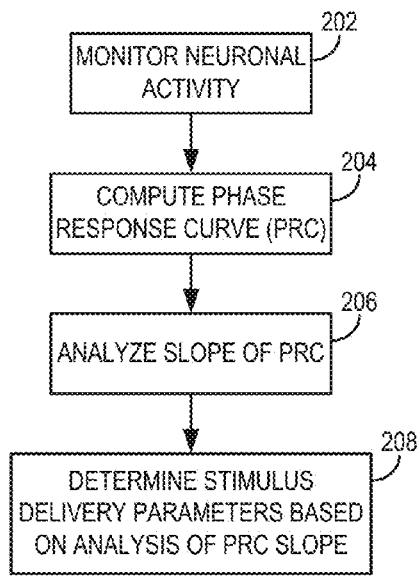
FIG. 2 is a flowchart setting forth the steps of an example method for determining optimized settings for a closed-loop stimulation system to deliver electrical stimulation, in which the settings are determined based on an analysis of a phase response curve estimated from measured electrophysiological activity.

Referring now to FIG. 2, a flowchart is illustrated as setting forth the steps of an example method for determining optimal settings for a closed-loop stimulation system, such as a deep brain stimulation system, based on an analysis of a phase response curve. Because the method is implemented in a closed-loop system, the stimulation settings can be updated in real-time in response to subject-specific conditions. The method includes monitoring electrophysiological activity using the closed-loop stimulation system, as indicated at step 202. Electrophysiological activity can include electrical activity associated with neurons (e.g. neuron firing), electrical activity associated with other nerves (e.g., nerves in the central or peripheral nervous system), and electrical activity associated with muscles.

A phase response curve is estimated from the measured electrophysiological activity, as indicated at step 204. In some embodiments, the phase response curve can be estimated from periodic electrophysiological activity, such as periodically firing neurons. In some other embodiments, the phase response curve can be estimated from a population oscillation.

One example of estimating the phase response curve from periodic electrophysiological activity, such as from periodically firing neurons, is provided as follows. A phase response curve can be estimated by looking at the change in phase following a stimulation from the expected phase of the unperturbed oscillation. This can be done for the local field potential by fitting a sinusoid to the data prior to the stimulation $$S_{pre}(t) = \sin(t \times f + \phi_{pre}) \quad (3).$$

where f is the frequency of the input, t is time, and $\phi$ is the phase of the stimulus. Another sinusoid is fit following the stimulation:

$$S_{post}(t) = \sin(t \times f + \phi_{post}) \quad (4).$$

The phase shift caused by the stimulation is the difference in the phase between the pre and post stimulation estimation of the phase at time of the stimulus:

$$\Delta\phi = \phi_{pre} - \phi_{post} \quad (5).$$

Figure 13A:
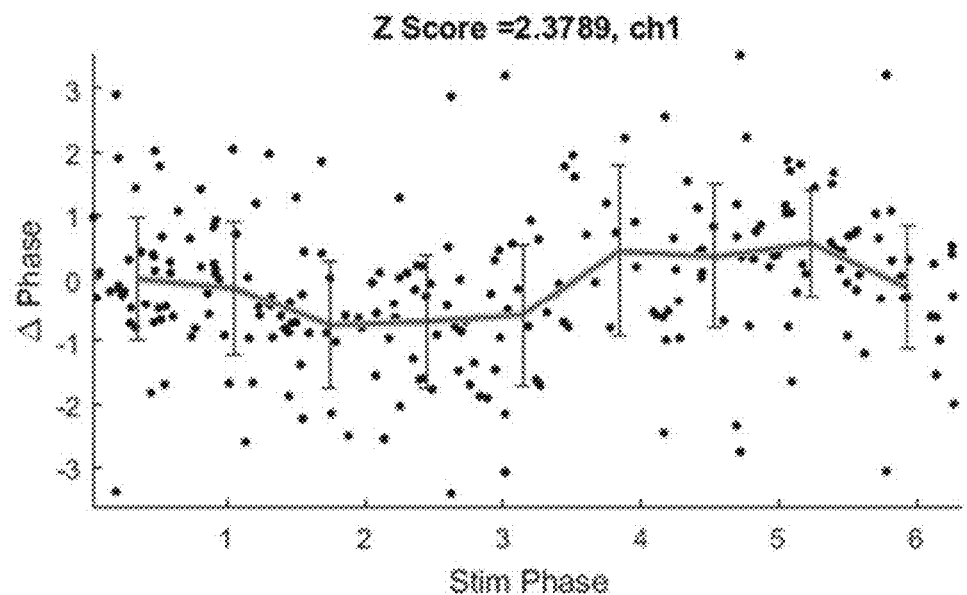
FIGS. 13A-F provide phase advance Δ versus stimulus phase for channels corresponding with contacts 1, 4, 5, 6, 7, and 8, respectively.
Figure 13B:
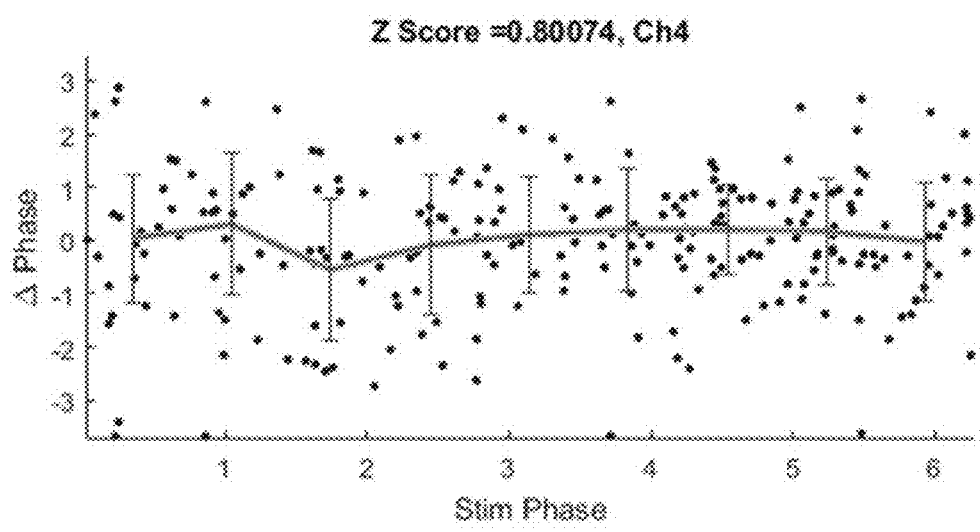
Figure 13C:
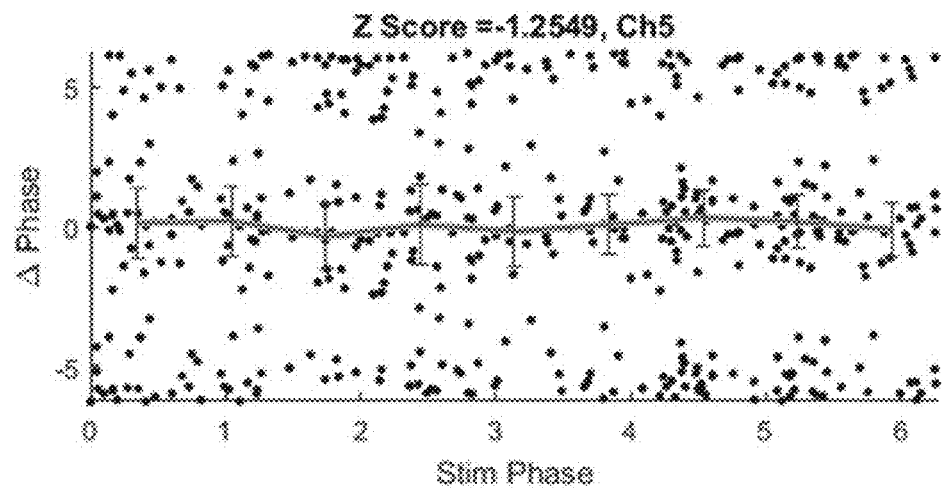
Figure 13D:
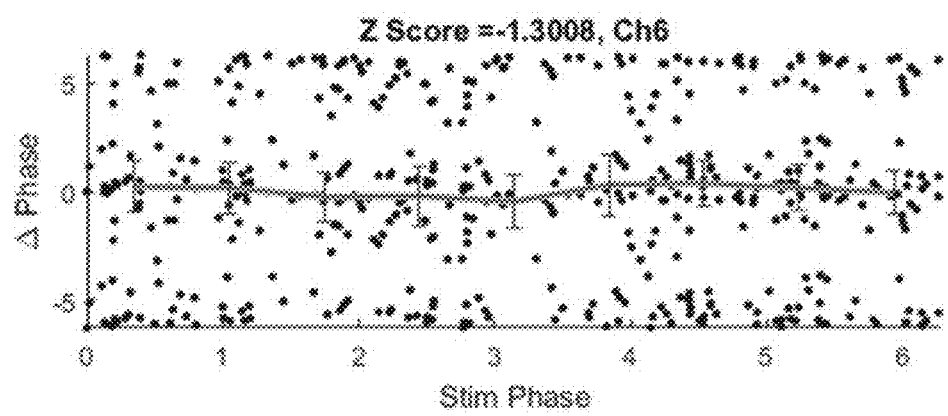
Figure 13E:
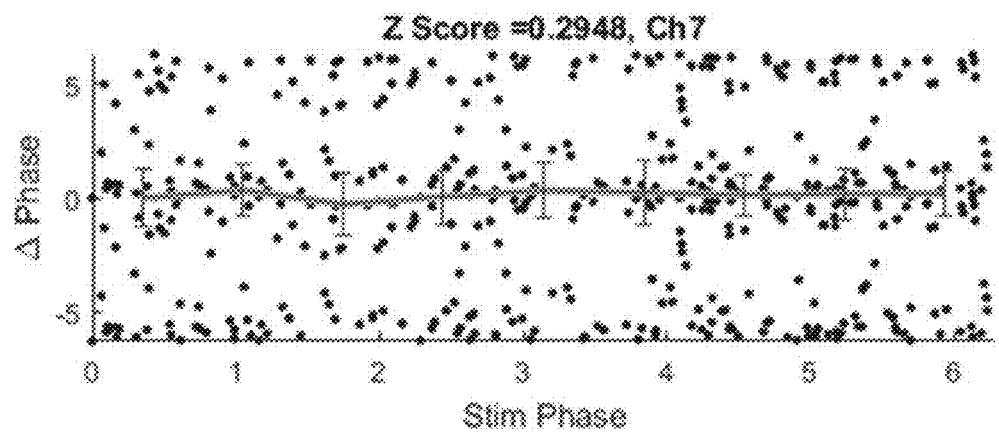
Figure 13F:
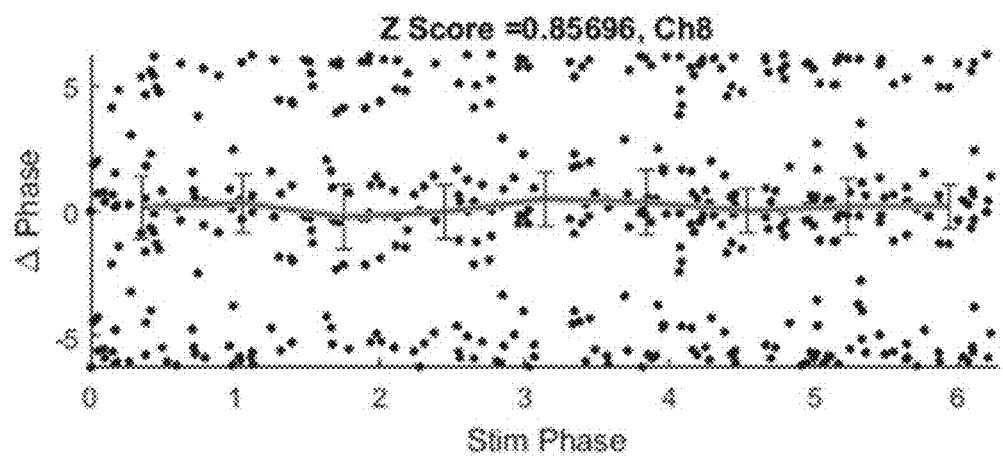
Figure 14:
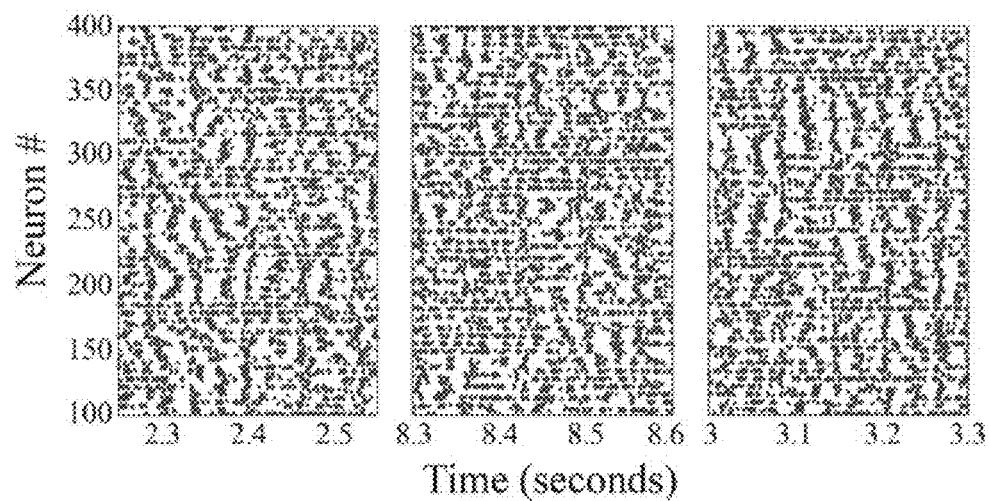
FIG. 14 includes rastergrams from the external globus pallidus of the Hahn & McIntyre model. It provides raw data showing that applying a burst of three equally spaced stimulus pulses (5 ms apart) triggered off of the phase of the oscillation more strongly modulates the 34 Hz oscillation. Left: No stimulation. Middle: Closed-loop phasic burst stimulation at a phase which disrupts the 34 Hz oscillation (phase=0.3). Right: Closed-loop phasic burst stimulation at a phase which enhances the 34 Hz oscillation (phase=0.7).

The PRC is then estimated from the change in phase as a function of the phase at the time of the stimulus estimated from the pre-stimulus phase:

$$Z(\phi) \equiv \Delta\phi = f(\phi_{pre}) \quad (6).$$

where $f(\phi)$ is a function, such as a polynomial, that is fit to the measured data to minimize the error between the measured phase change as a function of the stimulus phase. This change in phase is then estimated when the stimulus is applied at different phases of the oscillation. An example of a PRC estimated from the local field potential in the brain of a non-human primate model of Parkinson's Diseases is shown in FIG. 13A.

Referring again to FIG. 2, after the phase response curve is estimated, it is analyzed to determine an optimal phase window during which phasic stimulation should be applied by the closed-loop stimulation system to achieve a desired entrainment effect, as indicated at step 206. In general, the effect of a particular phasic stimulation on the ability of a neuron to synchronize to an oscillatory input can be predicted based on the estimated PRC. The optimal phase window can be determined based on the phase advance resulting from a particular phasic stimulation (e.g., a burst of stimulus pulses).

In some embodiments, the phase advance can be calculated by integrating the slope of the PRC over the phase range of the burst, starting at the onset of the burst, $\phi_{start}$, to the end of the burst, $\phi_{end}$, as follows:

$$\hat{Z}'(\phi_{start}) = \int_{\phi_{start}}^{\phi_{end}} Z'(\tau) d\tau. \quad (7)$$

Where $\hat{Z}(\phi)$ represents the PRC caused by stimulation over a range of phases given the PRC, $Z(\phi)$ estimated from a single input and $\hat{Z}'(\phi)$ and $Z(\phi)$ are the respective derivatives of those functions. When $\hat{Z}'(\phi_{start})$ is negative, the applied stimulus will enhance entrainment of the neuron to the sine wave input, and when $\hat{Z}'(\phi_{start})$ is positive, the applied stimulus will decrease the entrainment of the neuron to the sine wave input.

In some other embodiments, the phase advance can be calculated by further taking into account the phase advance induced by each applied stimulus in the burst. As an example, the effect on the phase difference for three equally spaced pulses can be calculated as follows, $$\varepsilon_{i+1} = \varepsilon_i \cdot Z_1 \cdot Z_2 \cdot Z_3 \quad (8);$$

where, $$Z_1 = (1 + Z'(\phi))$$

$$Z_2 = (1 + Z'(\phi_i + Z(\phi_i) + \gamma))$$

$$Z_3 = (1 + Z'(\phi_i + Z(\phi_i) + Z(\phi_i + Z(\phi_i) + \gamma) + 2\gamma)) \quad (9);$$

and where $\varepsilon'_{i+1}$ is the distance between two neurons after the three stimuli, $\varepsilon$ is the starting distance between two neurons, and $\gamma$ is the interstimulus interval ("ISI"). An implementation of this three-pulse burst is illustrated in the bottom right panel of FIG. 1. While Eqns. (8) and (9) solve for the effect on synchrony after three stimulus pulses, the equations can be generalized to any number of pulses.

It is noted that with Eqn. (9), each stimulus is treated as being independent in its effect from other stimuli. However, in reality, multiple stimuli are not expected to be entirely independent, such that, for example, a first stimulus may have a slightly different response from a second stimulus, which can have a different response from a third stimulus, and so on. If these changes are accounted for, a more accurate prediction can be achieved, as discussed in the context of Eqn. 10.

Predicting the effect of stimulation on synchrony with the PRC. Using the PRC, the effect of phasic stimulation on the amplitude of a population oscillation can be predicted. The precise phase divergence can be calculated, taking into account the stimulus pulse interval, as follows:

$$\varepsilon_{i+1} = \varepsilon_i(1 + Z_1'(\phi_i))(1 + Z_2'(\phi_i + Z_1(\phi_i) + \delta))(1 + Z_3'(\phi_i + Z_1(\phi_i) + Z_2(\phi_i + Z_1(\phi_i) + \delta) + 2\delta)) \quad (10);$$

where $\varepsilon_{i+1}$ is the phase difference between two neurons after the three stimuli; $\varepsilon_i$ is the time difference between two neurons on their $i^{th}$ spike; $\delta$ is the inter-stimulus-interval; and Z1, Z2, and Z3 are phase response functions associated with the first, second, and third stimulus pulse, respectively. These functions may differ from each other if they explicitly account for higher order resetting characteristics resulting from pulsing history. While this equation solves for effect on synchrony after three stimulus pulses, the equation can be generalized to any number of pulses.

FIG. 1 assumes the effects of each stimulus input have dissipated by the time the next stimulus is applied, and that each stimulus pulse has the same effect on the phase of the oscillation. In this case, where only first order effects are considered, Z1, Z2, and Z3 are identical. However, there may be interactions between stimuli, or higher order effects. The first order PRC, measured by applying a single sub-threshold stimulus pulse at 2 Hz, as well as a PRC measured using a burst of 3 stimulus pulses, as was used for PhaBS simulations, can be used to address higher order effects.

Figure 15:
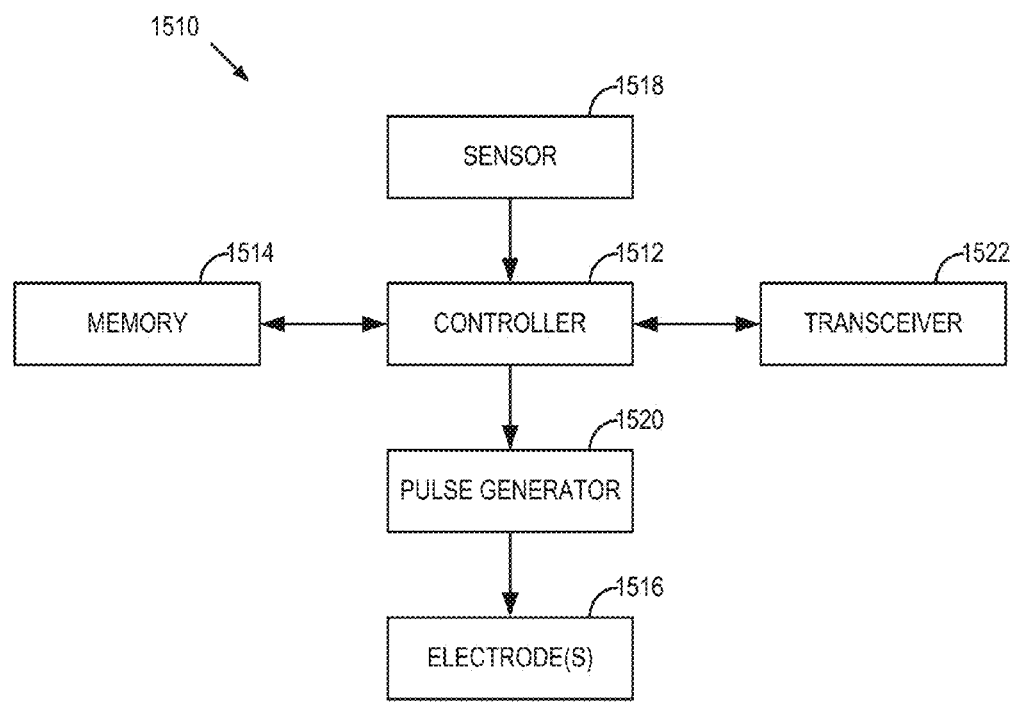
FIG. 15 is an example closed-loop stimulation system that can implement the methods described here.

Referring now to FIG. 15, an example closed-loop stimulation system 1510 that can implement the methods described above is illustrated. In general, the closed-loop stimulation system 1510 includes a controller 1512, a memory 1514, and at least one electrode 1516. The closed-loop stimulation system 1510 can be implemented as an implantable medical device, such as an implanted nerve stimulation system or an implanted cardiac rhythm management system.

In some embodiments, at least one electrode 1516 is capable of both sensing electrophysiological activity and delivering electrical stimulation. Thus, in these embodiments, the at least one electrode 1516 also forms at least one sensor. In other embodiments, one or more sensors 1518 may be separately provided.

The controller 1512 includes a processor to execute instructions embedded in or otherwise stored on the memory 1514 to implement the methods described above. The memory can also store measured electrophysiological activity data for processing, as well as settings to be provided to the controller 1512 for directing the at least one electrode 1516 to provide electrical stimulation to a subject.

At least one electrode 1516 operates under control of the controller 1512 to sense electrophysiological activity in a subject and to deliver electrical stimulations to the subject in response thereto. Sensing circuitry in the controller 1512 detects and processes electrophysiological activity sensed by the at least one electrode 1516 to determine the optimized phasic burst stimulation settings based on the methods and algorithms described above. The optimized phasic burst stimulation settings are provided as instructions to a pulse generator 1520, which in response to the instructions provides an electrical signal to the at least one electrode 1516 to deliver the electrical stimulations to the subject.

The closed-loop stimulation system 1510 can also include a transceiver 1522 and associated circuitry for communicating with a programmer or other external or internal device. As one example, the transceiver 1522 can include a telemetry coil.

In operation, the closed-loop stimulation system 1510 measures electrophysiological activity data by acquiring electrophysiological signals from the subject with the at least one electrode 1516. These electrophysiological signals are provided to the controller 1512 where they are processed. The controller 1512 analyzes the signals and estimates a phase response curve therefrom. The phase response curve is then analyzed to determine optimized settings for the delivery of electrical stimulation to the subject, as described above in detail. The optimized settings are provided to the pulse generator 1520 to control the at least one electrode 1516 to generate electrical stimulation that will achieve the desired effect in the subject, such as preventing an anticipated pathological electrophysiological event.

EXAMPLE

Single Cell and Computational Model Experiments

Materials and Methods

Slice Preparation. Brain slices containing the substantia nigra pars reticulata (SNr) were prepared using standard methods, such as those described, for example, by N. E. Hallworth, et al., in "Apamin-sensitive small conductance calcium-activated potassium channels, through their selective coupling to voltage-gated calcium channels, are critical determinants of the precision, pace, and pattern of action potential generation in rat subthalamic nucleus neurons in vitro," *The Journal of Neuroscience*, 23(20):7525-7542, 2003. Brain slices were prepared from Sprague Dawley rats aged 18-25 days. The animals were deeply anesthetized using isoflurane before being perfused transcardially with 10 ml of ice-cold artificial cerebral spinal fluid (aCSF) composed of (in mM): 126NaCl, 26NaHCO$_3$, 10 D-glucose, 2.5KCl, 1.25NaH$_2$PO$_4$, 2CaCl$_2$, and 2MgSO$_4$. Following decapitation, the animals' brains were extracted and chilled in aCSF. Sagittal slices 300 μm thick were cut using a Vibratome 3000 in a high-sucrose cutting solution continuously oxygenated with 95% O$_2$ and 5% CO$_2$. Slices were incubated in oxygenated aCSF at room temperature for at least one hour.

Electrophysiology Recording. Slices were placed in a recording chamber perfused with oxygenated aCSF at 36° C. Slices were visualized using differential interference contrast optics (Olympus, Center Valley, Pa.). Recording electrodes (3-8 MΩ) were pulled from borosilicate glass (P-97 micropipette puller; Sutter Instrument). Electrodes were back filled with intracellular fluid containing (in mM): 120 K-gluconate, 10 HEPES, 1 EGTA, 20KCl, 2MgCl$_2$, 2Na$_2$ATP, and 0.25Na$_3$GTP, and then filled with intracellular fluid containing 0.5 g/ml of gramicidin-D. Cells in the SNr were recorded from using a perforated-patch technique.

The SNr is a major output nucleus of the basal ganglia. While it is not clear where pathological oscillations in Parkinson's disease are generated, the output signal sent from the basal ganglia to the thalamus and on to motor cortex, is contemplated to be a signal that influences motor output. Disrupting synchrony in the output from the basal ganglia may be effective at suppressing the oscillatory signal sent to motor cortex, which is why this target was selected.

Data were recorded using a current-clamp amplifier (MultiClamp 700B; Axon Instruments, Molecular Devices, Sunnyvale, Calif.), sampled at 5 kHz, and collected using the publicly available Real-Time eXperimental Interface (RTXI) software (www.rtxi.org). Stimulation was applied through the patch-clamp electrode.

Burst Stimulation. To simulate a population oscillation to which a neuron could synchronize, a sine wave (400-1000 pA) was applied through the patch clamp electrode. Prior to applying the stimulus, the natural firing rate of the neuron was measured, and the sine wave was applied at the frequency of the firing rate. To investigate how stimulating at a specific phase affects how well a neuron is able to entrain to the sine wave, a burst of stimulus pulses (100-200 Hz) starting at different phases of the sine wave were applied through the patch clamp electrode on top of the sine wave. The burst duration lasted for 30% of the sine wave. This results in a different number of stimulus pulses depending on the natural firing rate of the neuron and frequency of the burst stimulus, resulting in 4-6 pulses per cycle on average. Stimulus pulses were applied starting at nine different phases from 0.1-0.9 of the period of the sine wave. For each phase, at least 30 cycles of phasic stimulation were applied followed by 30 cycles without phasic stimulation. The sequence of stimulation phases was randomized.

Estimating Synchrony from Experimental Data. To estimate entrainment of the neuron to the sine wave, a modified normalized entropy measure was used. Synchrony values (1-Entropy) calculated from spike density histograms (FIG. 3) were used to compare how well a neuron was entrained to the sine wave for each stimulus phase. P(i) is the probability of a neuron ring in a given phase bin, i, where B is the total number of equally spaced bins dividing up the sine wave. Using this, the entropy can be calculated from each spike density histogram. To account for the different number of spikes in each trial, an entropy bias correction was used:

$$Entropy_{Bias} = \frac{B-1}{2N}. \tag{11}$$

The unbiased entropy was normalized by the maximum entropy to get the normalized unbiased entropy value:

$$NormEntropy = \frac{\sum_{i=1}^{B} P(i)\ln P(i) - Entropy_{Bias}}{B\ln\frac{1}{B}}. \quad (12)$$

Standard deviations were calculated for each entropy value:

$$\sigma_{entropy} = \sqrt{\frac{1}{N}\sum_{i=1}^{B}(\ln(1-P(i)) + Entropy)^2 P(i)(1-P(i))}. \quad (13)$$

Statistical comparisons between entropy values were made using the Student's t-test, and p values<0.05 were considered significant. In some instances, it was found to be more natural to present the effect of phasic stimulation using a synchrony measure instead of entropy. Synchrony can be defined as, $$Synchrony \equiv 1 - NormEntropy \quad (14)$$

Computational Model. In the cellular experiments, how phasic stimulation prevents a neuron from synchronizing to a population oscillation was investigated. To test whether phasic stimulation could desynchronize neurons, a physiologically realistic network model of deep brain stimulation ("DBS") for Parkinson's disease described by P. J. Hahn and C. C. McIntyre in "Modeling shifts in the rate and pattern of subthalamopallidal network activity during deep brain stimulation," Journal of Computational Neuroscience, 28(3):425-441, 2010, was used. This model included 500 single compartment conductance-based neurons: 100 globus pallidus internal neurons (GPi), 100 subthalamic nucleus (STN) neurons, and 300 globus pallidus external (GPe) neurons, with spike train input from the cortex and striatum. Parameters for both a healthy and Parkinsonian state were fit using data from non-human primates. STN DBS was applied in the model by activating STN efferent paths and applying subthreshold current to subthalamic neurons. This model spontaneously generates a 34 Hz oscillation in the Parkinson's disease state.

To test the closed-loop phasic stimulation protocol, a real-time estimation of the population phase was required. This was estimated by a time-weighted Fourier transform of the spikes occurring in the previous T=400 ms at frequency, ω=34 Hz:

$$X(f, t) = \sum_{k=1}^{N_s} e^{\frac{(S_k-t)}{\tau}} e^{-2\pi j f S_k}; \quad (15)$$

where $S_k$ is the time of the $k^{th}$ spike of the GPe population, $N_S$ is the number of spikes in GPe from time t=400 ms until the present time, t, and τ=3 defines the time constant of the time-weighting of the fit.

The instantaneous phase at time t, φ(t) is defined as:

$$\phi(t) = \angle\left(\sum_{f=f_{min}}^{f_{max}} X(f, t)e^{2\pi jtf}\right); \quad (16)$$

where f is the frequency range of the beta oscillation, $f_{min}$=30 Hz, and $f_{max}$=36 Hz.

Stimulation was applied at a different delays after the midpoint of the oscillation was detected (i.e. where φ(t)=0). Simulations were run for 10 delay values. A single stimulus pulse as well as bursts of three equally spaced stimulus pulses were applied. The power of the pathological beta oscillation (31-36 Hz) from a baseline gamma (60-64 Hz) was measured at each stimulation phase.

Results

It was hypothesized that the PRC can be used to predict a phase range over which a burst of stimulus pulses can be applied to disrupt entrainment of neurons to a population oscillation. First, this was tested in vitro in single neurons, and then in a population oscillation in a computational model of the basal ganglia. The PRCs were used to predict phases of the oscillation in which stimulation enhances or disrupts entrainment of the neuron. The PRCs were also used to determine the optimal burst frequency to disrupt an emergent pathological population oscillation.

Phasic stimulation effects on single neuron entrainment to an oscillatory input. The effect of phasic burst stimulation on a neuron's ability to phase lock to an oscillatory input was investigated in 18 cells in the SNr in rat brain slice. This is a major output nucleus of the basal ganglia network. An oscillatory current was applied at the natural frequency of the neuron to simulate a population oscillation. The stimulus amplitude and the input frequency were adjusted so that the neuron was moderately entrained to the oscillation, allowing for stimulation to either increase or decrease entrainment to the oscillation. Significant entrainment to the oscillation was seen in 15 neurons; however, in three cells, the amplitude of the oscillation was too low or the neuron was not firing periodically enough to elicit significant entrainment (t-test, p<0:05). On top of the oscillatory input, a burst of stimulus pulses at 100-200 Hz was applied for 30% of the period, starting at a specific phase of the oscillatory input.

Figure 3:
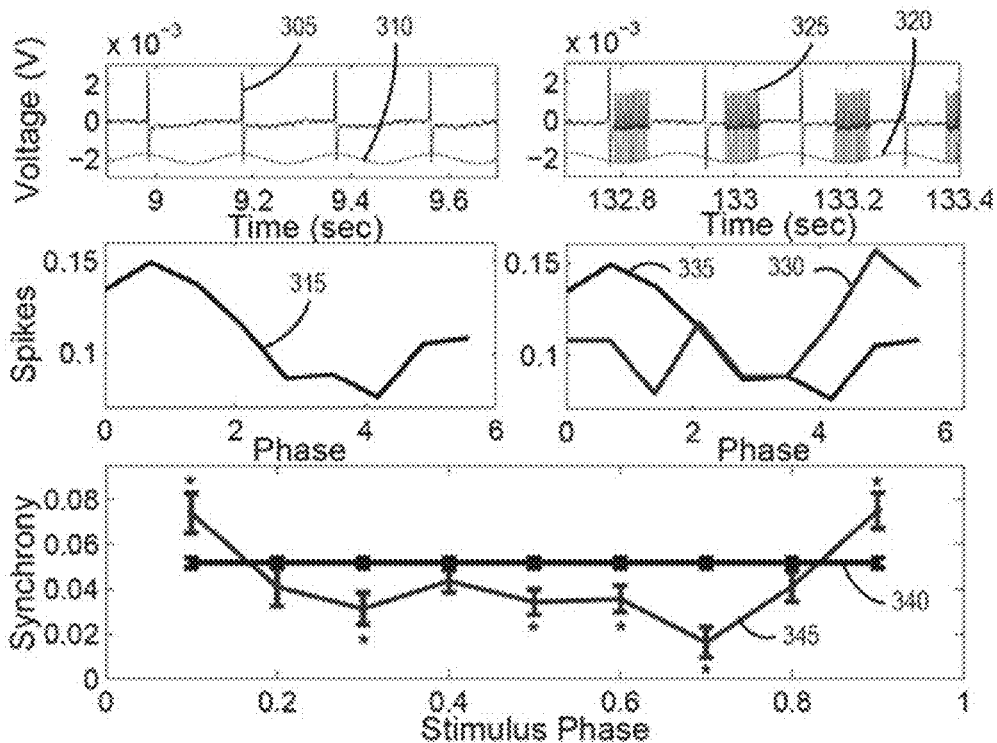
FIG. 3 illustrates example data from a substantia nigra pars reticulata cell. Top left: Voltage trace of neuron (trace 305) and oscillatory current input (wave 310). The neuron is phase locked to the oscillation. Below: spike density histograms (315) showing the number of spikes occurring at each phase of the sine wave. It can be seen that the neuron prefers to fire early in the phase of the oscillatory input. Top right: Oscillatory input (320) and phasic burst stimulation applied at 0.7 of the phase (325). Burst stimulation at this phase prevents the neuron from locking to the oscillation. Below: spike density histogram provided with the phasic stimulation (330) is flatter compared to the oscillatory input alone (335), indicating that the phasic burst stimulation decreases synchrony. A peaked histogram indicates strong entrainment; a flat histogram indicates low entrainment. Bottom: Summary of synchrony calculated from the spike density histograms. The line 340 is the mean and standard deviation estimated from synchrony due to oscillatory input alone (this is same value across all phases), the line 345 shows the synchrony values as a function of the burst phase onset (Stimulus Phase or "StimPhase"). Asterisks indicate stimulation significantly modulated entrainment from baseline (* $p<0.01$).

The effect that the starting phase of the burst of stimulus pulses had on how well the neurons phase locked to the oscillatory input was investigated. An example from one neuron is shown in FIG. 3. In this example, a comparison between burst stimulation off and burst stimulation applied at a phase which disrupted the ability of the neuron to entrain to the oscillation is shown. In the absence of burst stimulation, the neuron was relatively entrained to the oscillation. Stimulus phase modulated the ability of the neuron to entrain to the oscillation. In this neuron, stimulation applied at a phase of 0.7 disrupted entrainment while stimulation applied at a phase of 0.1 enhanced entrainment. Significant modulation of entrainment as a function of burst phase onset was seen in all cells (ANOVA, p<0:05). However, in two neurons only an increase in synchronization was observed, indicating that these neurons most likely changed their natural frequency over the duration of the experiment and the baseline synchronization measured was no longer accurate. These cells were eliminated from further analysis.

It was also tested if the PRC can be used to predict the effects of stimulus phase on the ability to enhance or disrupt entrainment to the oscillatory input. The effect of stimulation at each phase was predicted by integrating the slope of the PRC over the phase range for which the stimulus burst was applied, as described above, using Eqn. (7). If the average slope of the PRC was negative, burst stimulation was predicted to increase entrainment to the oscillation; if the average slope was positive, stimulation was predicted to disrupt entrainment.

Figure 4:
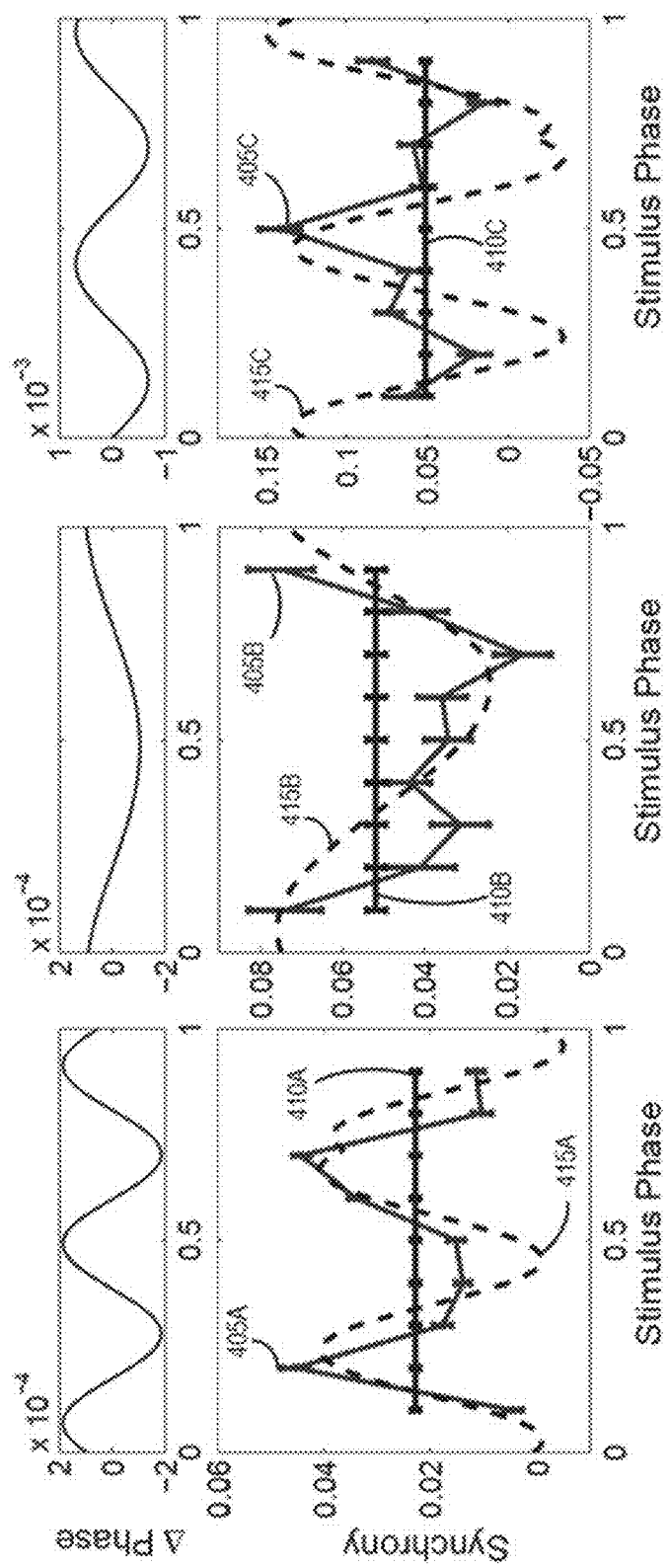
FIG. 4 illustrates using the phase response curve to predict experimental synchrony values from cells in the substantia nigra pars reticulata. Top: Phase response curves (PRCs) for each cell. Bottom: Lines 405A-C: Experimental values of synchrony as a function of the phase of burst stimulation. Horizontal lines 410A-C: Synchrony value with burst stimulation off. Black dotted lines 415A-C: Values of synchrony predicted from the PRC of the neuron, $-\check{Z}'(\phi_{start})$.

The predicted modulation on entrainment was compared to the measured effect of phasic stimulation; examples from three neurons are shown in FIG. 4. In these examples, it can be seen that the predicted modulation of synchrony $-\hat{Z}'$ ($\phi_{start}$) matched the measured synchrony quite well. Notice that the negative of the average slope was plotted to match the synchrony measure. Peaks in the expected synchrony occurred at phases of stimulation where the average slope was the most negative, and lowest synchrony occurred when the average slope was most positive.

Figure 5:
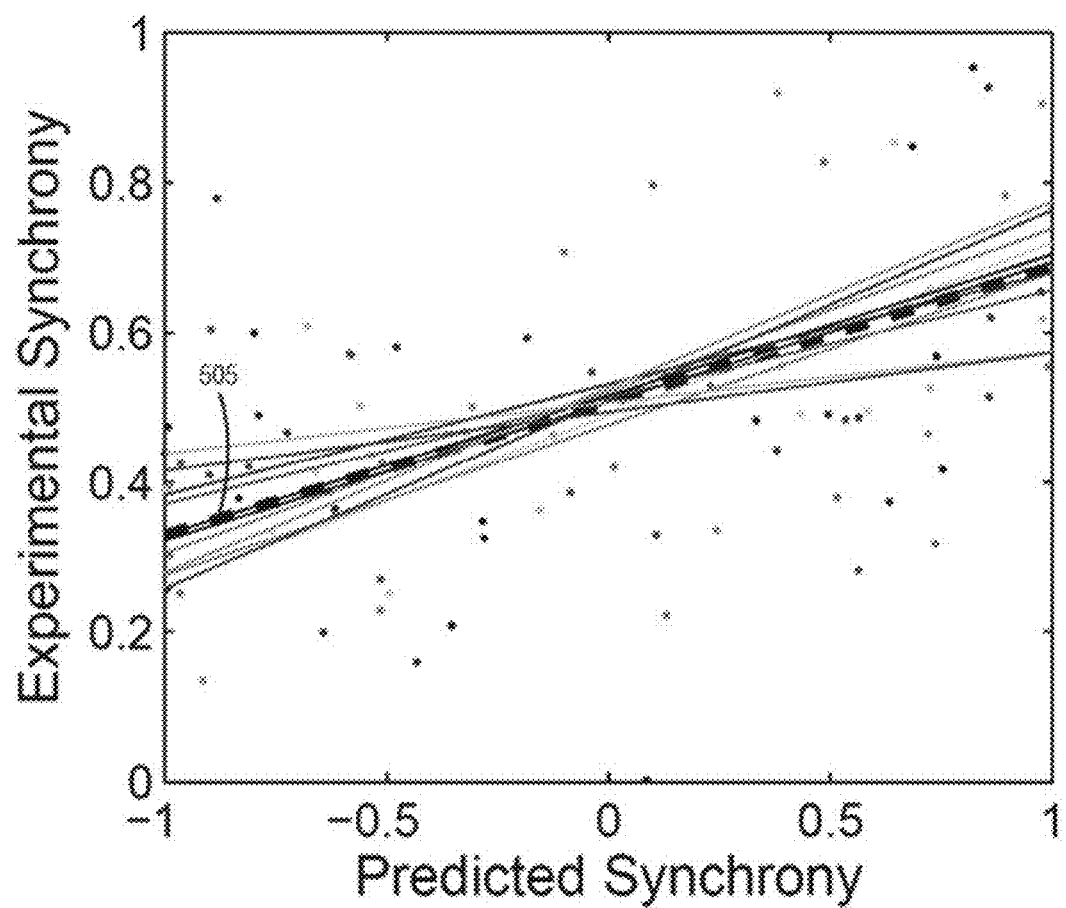
FIG. 5 illustrates correlations between experimental and predicted synchrony across all cells. Plot of experimental synchrony compared to predicted synchrony at each stimulus phase for each cell, with a regression line fit to each cell. Each of the 13 cells is represented with a different shade. The dashed line 505 represents the regression fit using all cells, $R^2=0.53$.

To summarize the single neuron findings, the correlation between experimental synchrony and predicted synchrony across all nine phases for the 13 cells that were found to have significant stimulus phase dependent modulation were plotted. FIG. 5 shows the measured synchrony versus the predicted synchrony. The correlation coefficient (Pearson R value) across all cells was R=0.53 (significant at p<0.01), indicating that 28% ($R^2$=0.28) of all variance in synchrony can be explained by the stimulus phase.

Phasic Stimulation Effects on Population Oscillation Strength. While stimulation locked to the phase of an oscillation can prevent a neuron from synchronizing to the population, it does not directly test the hypothesis that phasic stimulation can decrease synchrony in a population oscillation. To test this hypothesis, a physiologically realistic computational model of the basal ganglia was used. A schematic of this model is illustrated in FIG. 6A.

Figure 6A:
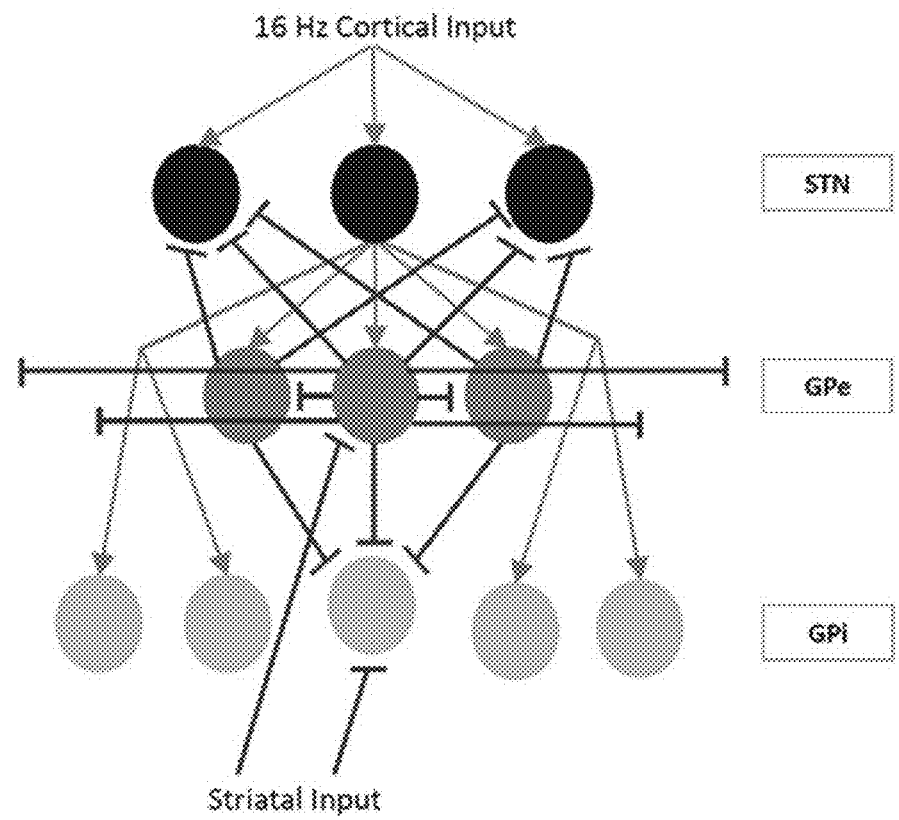
FIG. 6A illustrates connectivity of a Hahn and McIntyre model including 300 conductance based neurons in the globus pallidus external (GPe), 100 neurons in the subthalamic nucleus (STN), and 100 neurons in the globus pallidus internal (GPi).
Figure 6B:
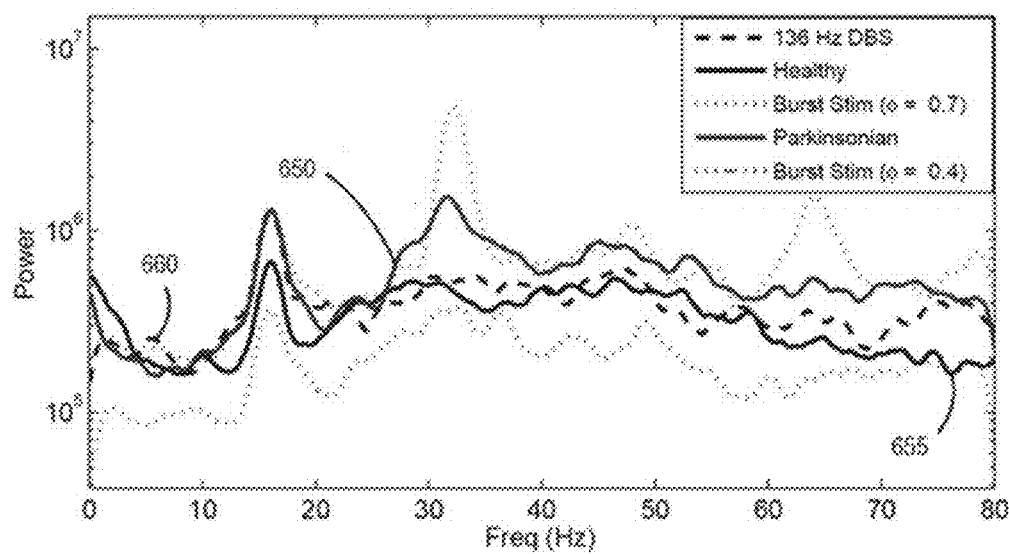
FIG. 6B illustrates a power spectrum for the Hahn and McIntyre model of FIG. 6A showing the emergence of a 34 Hz pathological oscillation in the parkinsonian state (line 650), which is not present in the healthy state (line 655) and is suppressed with 136 Hz DBS (dotted line 660). The peak at 16 Hz is caused by the cortical input into the network model.

In the model shown in FIG. 6A, an oscillation centered around 34 Hz, termed the beta oscillation, emerged from the interaction between the excitatory population in the STN and the inhibitory population in the GPe, as can be seen in the power spectrum calculated from the spike times in FIG. 6B.

Figure 7:
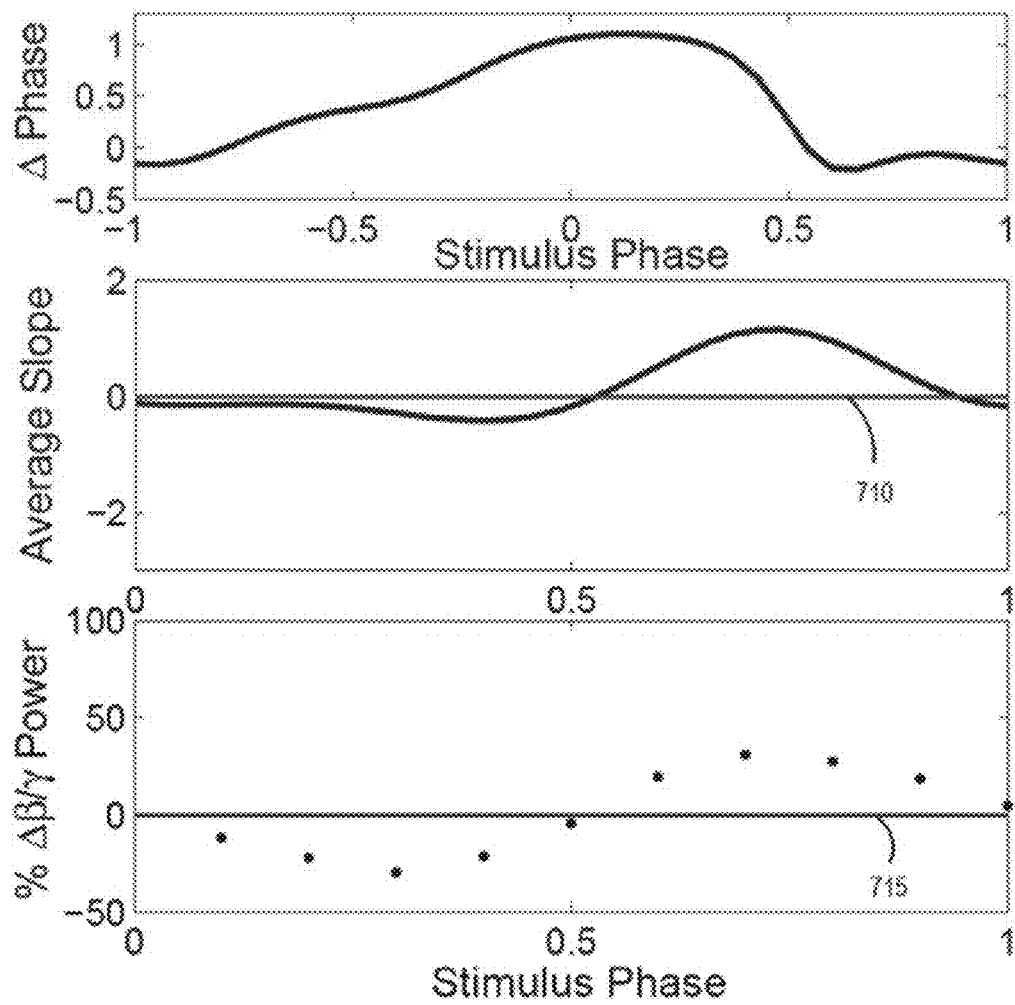
FIG. 7 illustrates effects of phasic stimulation with a single pulse on the population oscillation can be predicted using the PRC. Top: Population PRC. Middle: Single pulse predictions determined from the slope of the PRC. Prediction of which stimulus phases will desynchronize the population oscillation (below the horizontal line 710) and which will enhance the oscillation (above the horizontal line 710). Bottom: Ratio of Beta (31-36 Hz) to Gamma (60-64 Hz) power as a function of the stimulus phase, shown as a percent change from stimulation off condition (line 715). Stimulating early in the phase suppresses the 34 Hz oscillation, while stimulating late in the phase enhances it.

By measuring the PRC from the population oscillation to the DBS pulse, shown in the top of FIG. 7, the stimulation frequencies that suppress and enhance the oscillation can be predicted. It was hypothesized that there is a phase dependent effect of stimulation on the population oscillation, that the population PRC can be used to predict these effects, and that a burst of stimulus pulses over a range of phases predicted to disrupt the oscillation would be more effective at disrupting the oscillation than a single stimulus pulse.

In order to implement a closed-loop phasic stimulation protocol in the computational model, an estimate of the instantaneous phase of the pathological oscillation was needed. A time-weighted Fourier transform of the spike trains was used to estimate the instantaneous phase of the population oscillation. This phase estimation was used to trigger the stimulus. First, a single phasic stimulus pulse was applied and then a burst of three stimulus pulses.

For a single stimulus pulse, the effects of stimulation phase on the power of the pathological oscillation (shown in FIG. 7) can be predicted from the population PRC. Stimulation occurring early in the oscillation was capable of disrupting the 34 Hz oscillation below baseline (DBS Off), while stimulation applied late in the oscillation enhanced the pathological oscillation. The ratio of beta to gamma power was measured as a function of stimulation phase and plotted as a percent change with respect to un-stimulated power at the bottom of FIG. 7. Using a small stimulus amplitude, a 30% reduction in the beta oscillation was seen at the optimal stimulus phase. These results were compared with predictions made using the PRC shown at the top of FIG. 7.

For the single pulse, predictions were made from the slope of the PRC. Early stimulus phases, which suppress the pathological oscillation in simulations, occurred when the slope of the PRC was positive, while late stimulus phases, which enhance the pathological oscillation occurred when the slope of the PRC was negative. Predictions made from the PRC, plotted as the negative slope of the PRC ($-\hat{Z}'(\phi)$) in the middle panel of FIG. 7, match well with the simulation results showing the percent reduction of the pathological oscillation (bottom of FIG. 7).

While a single pulse was effective at disrupting the emergent pathological oscillation, it was hypothesized that a burst of stimulus pulses over a range of phases will be more effective at disrupting the oscillation (see FIG. 1). To test this, a burst of three stimulus pulses triggered off of the instantaneous phase was applied to the computational model. The PRC was used to predict the burst frequency and stimulus phase, using Eqns. (8) and (9), that would produce the maximum suppression of the population oscillation. These equations were used to optimize both the phase, $\phi_i$, and the burst frequency ($\gamma$ is the time between pulses within the burst). Predictions of the stimulus effect on synchrony were made for a range of $\phi_i$ and $\gamma$ and shown as a grayscale map at the top of FIG. 8. Values above zero were predicted to suppress the oscillation, while values below zero were predicted to enhance the oscillation. Large modulations of the pathological oscillation with respect to stimulus interval were not predicted (i.e., a burst of stimulus pulses starting at a phase of 0.4 was predicted to disrupt the pathological oscillation for each stimulus interval represented).

Figure 8:
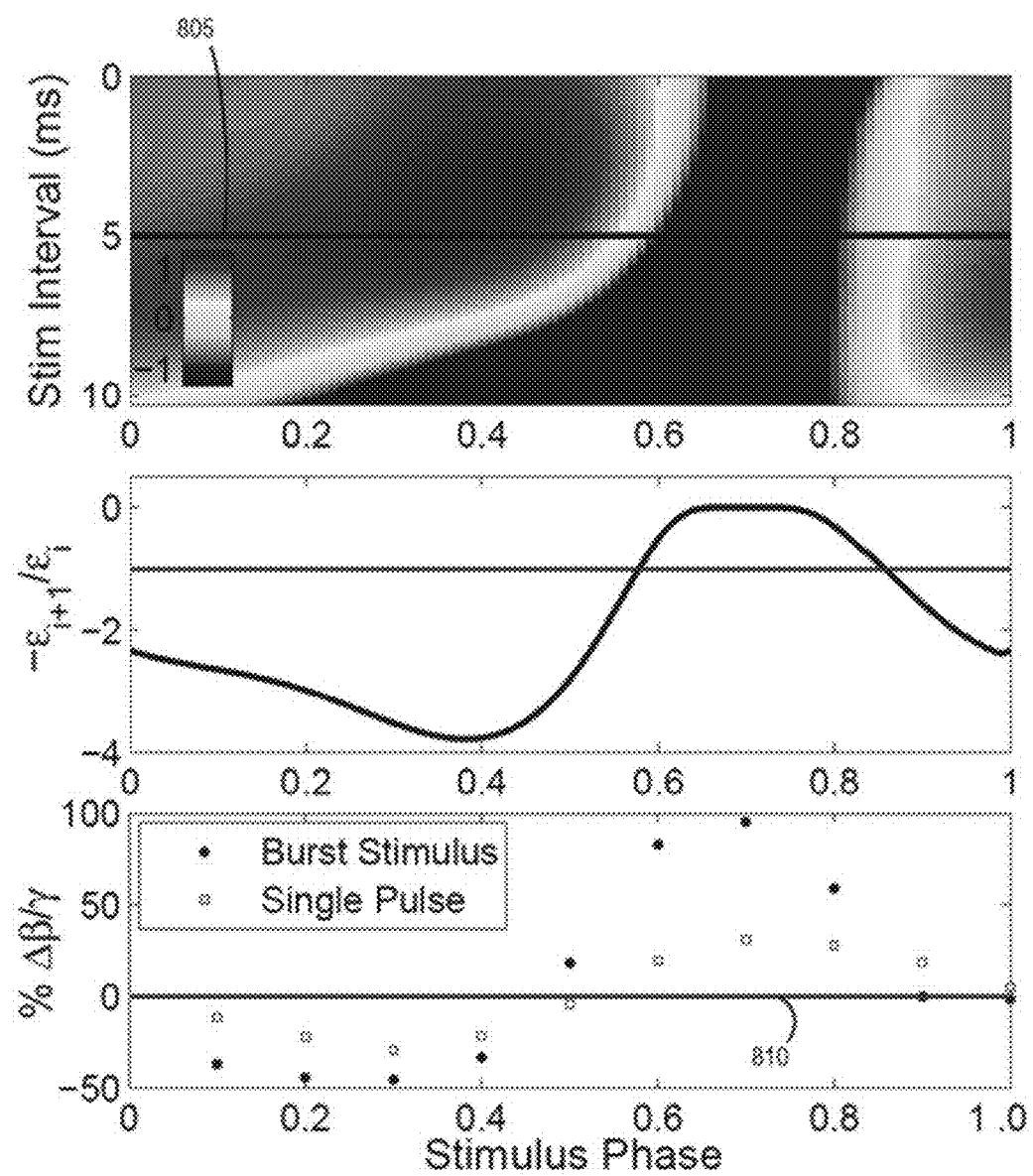
FIG. 8 illustrates that effects of phasic burst stimulation on the population oscillation are stronger than single pulse stimulation and optimal parameters can be predicted from the PRC. Top: Grayscale map showing predictions made from the population phase response curve. Predictions are made for stimulation phase and burst frequency. Values above zero are predicted to suppress the population oscillation, while values below zero are predicted to enhance the oscillation. Middle: Predictions of the phasic effect of burst stimulation at a 5 ms stimulus interval (line 805 in top graph). Bottom: Percent change in the ratio of beta (31-36 Hz) to gamma (60-64 Hz) power compared to DBS off (line 810) as a function of stimulus phase. Phasic burst stimulation (black circle) is compared to single pulse stimulation (open square). Burst stimulation has a stronger effect on power in the pathological population oscillation.

When simulations were run varying the stimulus interval while keeping the stimulus phase constant, a significant difference in the power of the pathological oscillation was not seen (data not shown). However, the map did predict a significant stimulus phase dependent modulation of the pathological oscillation. Predictions using an inter-stimulus-interval of 5 ms are shown in the middle panel of FIG. 8. Simulations were run using the same stimulus interval (5 ms) and predictions made from the PRC were compared to the beta-gamma ratio as a function of stimulus phase. Percent change with respect to un-stimulated power is shown at the bottom of FIG. 8; gamma power did not change with respect to stimulation phase (data not shown). Just as with the single pulse, there was a phase-dependent effect on the power in the pathological oscillation that can be predicted using the PRC (compare the middle of FIG. 8 to the bottom of FIG. 8). Therefore, the PRC can be used to predict the optimal stimulus phase and stimulus interval for a burst of stimulus pulses.

As predicted in FIG. 1, the effects of the burst stimulation are stronger than the effects of the single pulse stimulation, as seen in the bottom of FIG. 8. At certain phases, almost a 50% reduction in the power of the pathological 34 Hz oscillation is seen using a burst of stimulus pulses with significantly lower amplitudes (e.g., ten percent) of those previously used in clinical practice.

In this example, it was shown that the PRC can be used to predict phases for stimulation to optimally disrupt synchrony. This was tested and validated in vitro in single neurons as well as in a computational model of Parkinson's disease ("PD") with an emergent population oscillation. A closed-loop approach to suppress oscillations, termed Phasic Burst Stimulation ("PhaBS"), was proposed. In the proposed approach, the PRC was used to optimize both the stimulus phase and burst frequency. PhaBS was shown to be effective at disrupting entrainment of neurons phase locked to an oscillatory input, and at suppressing a population oscillation.

The burst stimulation was more effective than a single stimulus pulse in suppressing the population oscillation. This closed-loop approach has the potential to improve efficacy and robustness of deep brain stimulation and other closed-loop stimulation systems. While the foregoing example was focused on beta oscillations in PD, the approach can be used to disrupt or enhance other oscillatory biomarkers.

The PRC can be used to predict the effects of phasic stimulation on the amplitude of the 34 Hz oscillation (see FIG. 7). The PRC can be estimated by measuring the phase advance of the oscillation as a function of the stimulus phase using a single stimulus pulse per cycle. This slope of this first order PRC can be used to predict the phase dependent modulation of the 34 Hz oscillation seen using closed-loop phasic stimulation. While a single pulse per cycle was effective at disrupting the emergent pathological oscillation, a burst of stimulus pulses over a range of phases is expected to be more effective at modulating the oscillation (see FIG. 1). Roughly 30% of the first order PRC has a positive slope (see FIG. 7). The interstimulus interval of 5 msec was chosen so the three pulses covered about 30% of the period. As predicted in FIG. 1, the effects of burst stimulation are stronger than the effects of stimulation using a single pulse per cycle. With PhaBS, almost a 50% reduction in the power of the pathological 34 Hz oscillation compared to baseline (DBS off) is seen at the optimal phase (see FIG. 9).

In a first order approximation, the effects of each stimulus pulse on the phase advance was summed to account for the burst stimulation. When the PRC is measured using a burst of three stimulus pulses, the shape does not match this first order approximation PRC (see FIG. 9). This indicates that there are higher order effects, and that each stimulus pulse within the burst does not result in equal phase effects. For this reason, the PRC estimated using a burst of stimuli was used to predict the effects of PhaBS.

Figure 9:
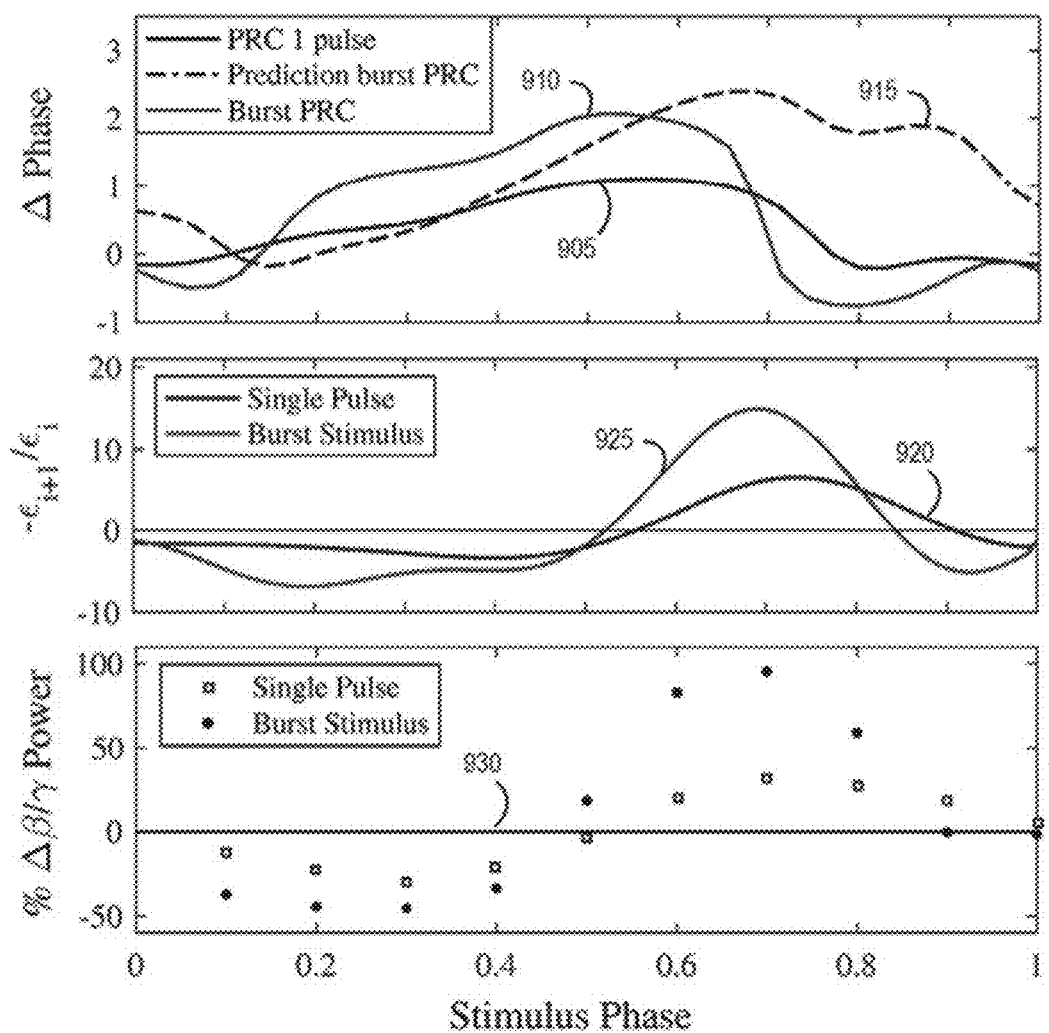
FIG. 9 illustrates the phase response curve (PRC) can be used to predict the effects of phasic stimulation on the 34 Hz parkinsonian oscillation seen in the Hahn and McIntyre model. Top: PRCs estimated using, 1 (solid line 905) and 3 (line 910) stimulus pulses per cycle. Assuming each no interactions between pulses, the PRC for three pulses is predicted (dotted line 915) from the single pulse PRC. The difference seen between the prediction (dotted line 915) and the PRC estimated using 3 pulses (line 910) indicates there are higher order effects. Middle: Predictions from the single pulse PRC (line 920) and the 3 stimuli PRC (line 925). Stimulating at phases where the curve is below zero is predicted to desynchronize the oscillation. Bottom: Ratio of Beta (31-36 Hz) to Gamma (60-64 Hz) amplitude as a function of stimulus phase, shown as a percent change from stimulation off (solid black line 930 at y=0). Stimulating early in the phase suppresses the 34 Hz oscillation, while stimulating late in the phase enhances it. This matches with predictions made using the PRC (middle). Furthermore, 3 pulses per cycle result in a stronger modulation of the 34 Hz oscillation.
Figure 10A:
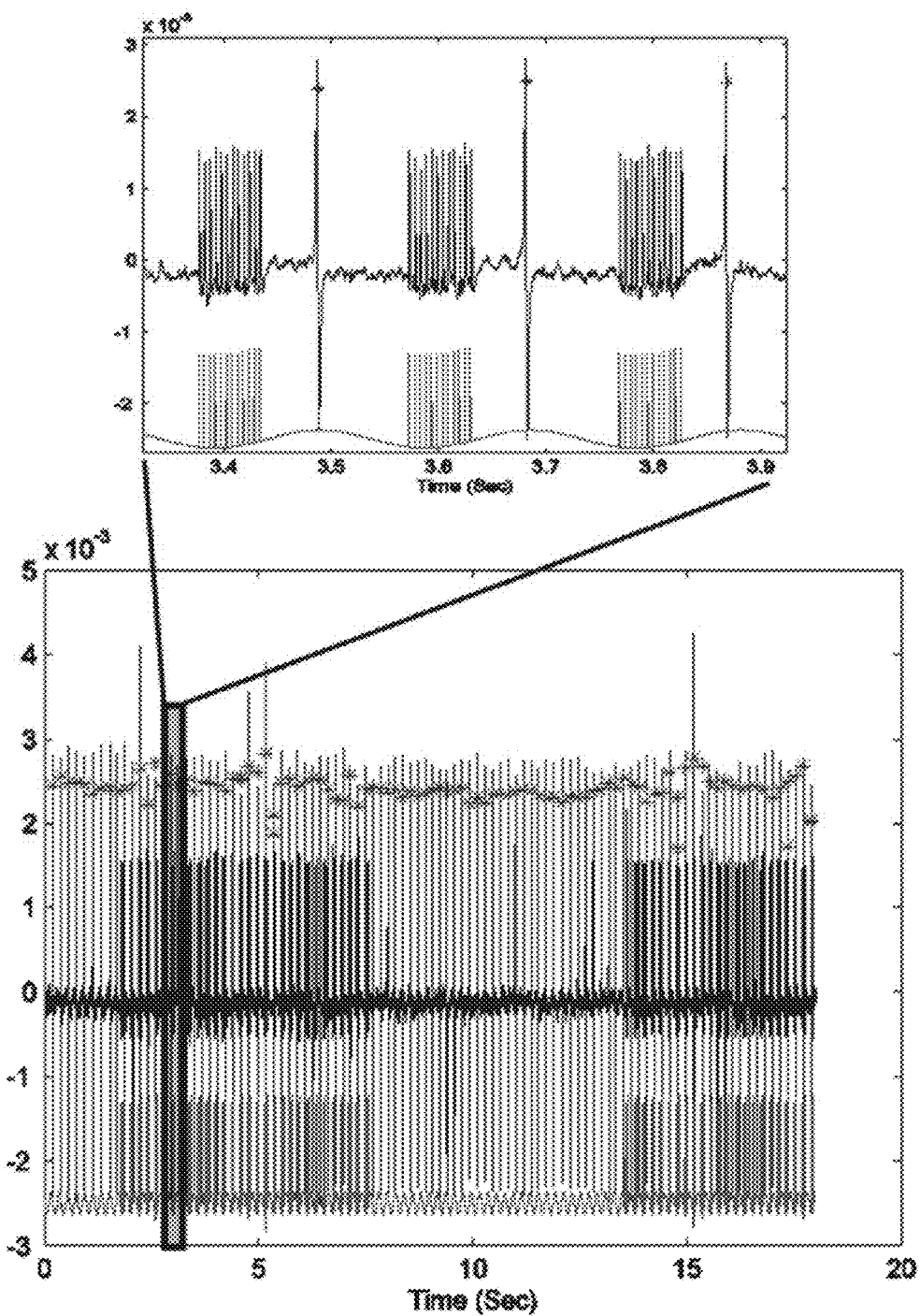
FIGS. 10A and 10B illustrate closed-loop phasic stimulation increases synchrony when applied at certain phases and decreases at others in single cell/slice data from a rat.
Figure 10B:
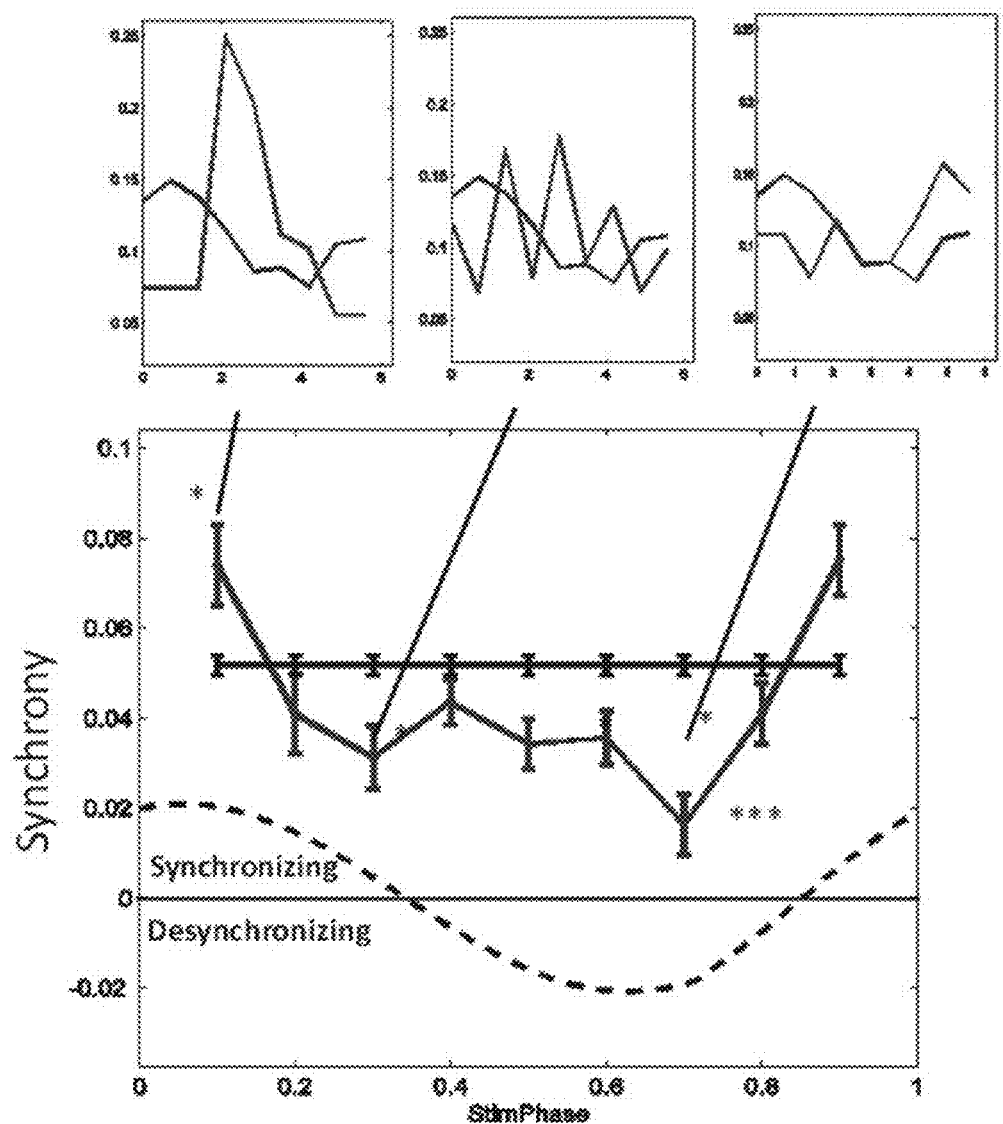
Figure 11A:
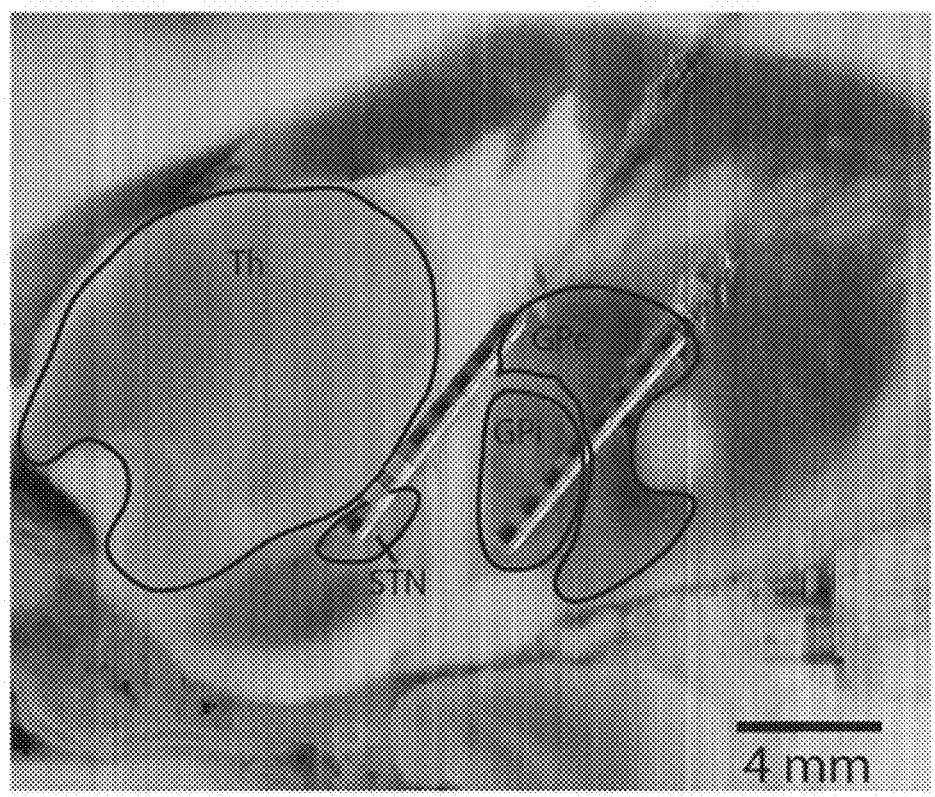
FIG. 11A shows placement of 8-contact DBS lead targeting the STN and the globus pallidus ("GP"). The STN is stimulated through contacts 2 and 3 at 600 µA.
Figure 11B:
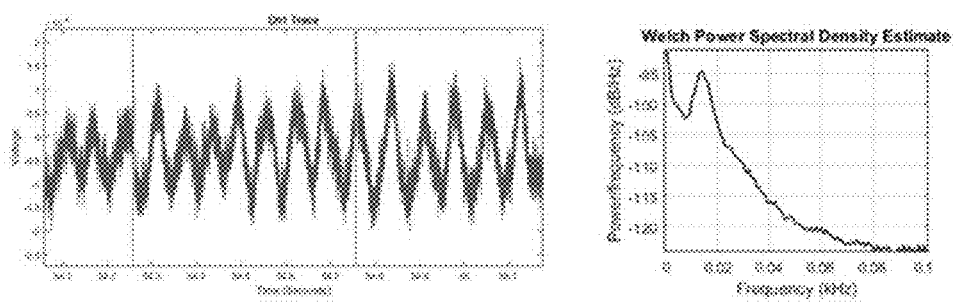
FIG. 11B provides the 14 Hz oscillation for channel 1 of the DBS lead of FIG. 11A (left), and the Welch power spectral density estimate (right).
Figure 12:
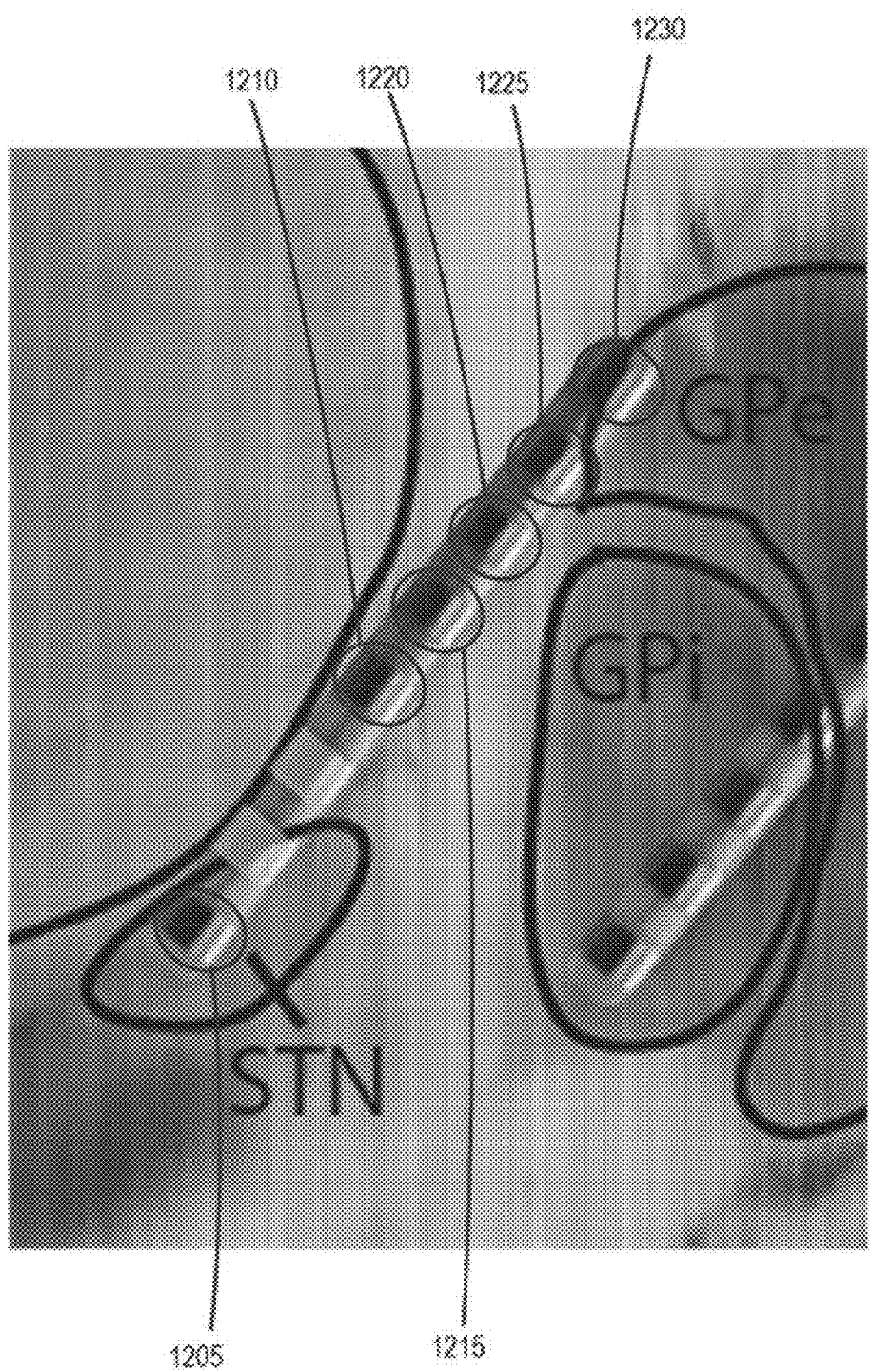
FIG. 12 is a close-up view of the DBS lead of FIG. 11A, showing contacts 1, 4, 5, 6, 7, and 8 labeled as 1205, 1210, 1215, 1220, 1225, and 1230, respectively.

The effects of PhaBS on the 34 Hz parkinsonian oscillation seen in the Hahn & McIntyre model can be predicted using the burst PRC (see FIG. 9). The slope of the burst PRC is positive when stimuli are applied at phases early in the oscillation, which was found to suppress the pathological oscillation in simulations. Stimulating late in the phase, which enhances the pathological oscillation in simulations, corresponds to phases when the slope of the PRC is negative. Predictions from the PRC, plotted as the negative slope of the PRC ($-Z'(\phi_i)$), are shown in the middle panel of FIG. 9. Negative values indicate phases predicted to desynchronize the oscillation. Further, the burst PRC predicts a larger modulation of the oscillation using PhaBS than when using a single pulse, and is validated in simulations. Predictions match well with the simulation results showing the percent reduction of the pathological oscillation (FIG. 9). The PRC was used to predict the stimulus phase using Eqn. (14) that would produce the maximum suppression of the population oscillation. This equation may be useful in optimizing both the phase, $\phi_i$, and the stimulus interval, $\delta$.

Phasic burst stimulation is a closed-loop technique that can be implemented, for instance, to treat PD using DBS. Currently, open-loop approaches are used to treat motor symptoms, where stimulation parameters are pre-programmed by a clinician and do not adjust in response to fluctuations in symptoms. While the open-loop approach is effective and used with most neurostimulation systems available, it may not be optimal. One limitation of an open-loop approach is that the same level of stimulation is applied regardless of the severity of a patient's motor symptoms. A closed-loop approach, however, offers many potential benefits by improving efficacy, reducing side effects, increasing battery life, and using a patient-specific physiological signals to systematically tune stimulation.

For phasic burst stimulation to be effective, an oscillatory biomarker, such as the beta oscillation in PD, is preferably modulated as a function of the stimulation phase. In order to determine optimal stimulation phase and burst frequency for phasic burst stimulation, a PRC is measured from the subject. Recently, it has been shown that it is possible to estimate PRCs from local field potential recordings from the STN of PD patients. This suggests that the pathological beta oscillation implicated in PD is sensitive to the phase at which a stimulus is applied.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for controlling a closed-loop stimulation system having one or more electrodes configured to apply stimulating electrical signals and to receive electrophysiological signals, the method comprising:
   a. measuring, with the one or more electrodes of the closed-loop stimulation system, electrophysiological signals from a subject;
   b. estimating a phase response curve from the measured electrophysiological signals;
   c. computing a slope of the phase response curve, wherein determining the electrical stimulation settings includes determining a phase window during which electrical stimulation is to be applied, wherein the phase window includes a range of phases during which the slope of the phase response curve has a positive slope;
   d. determining electrical stimulation settings based on the computed slope of the phase response curve; and
   e. controlling the closed-loop stimulation system to apply electrical stimulation based on the determined electrical stimulation settings.

2. The method of claim 1, wherein the system is a closed-loop deep brain stimulation system, and the electrophysiological activity signals are neural activity signals.

3. The method of claim 2, wherein controlling the stimulation system comprises applying an electrical stimulation to one or more neurons to suppress a pathological oscillation in the brain of the subject based on the slope of the phase response curve.

4. The method of claim 1 further including the step of applying a burst of electrical stimulation in the phase window.

5. The method of claim 1, wherein controlling the closed-loop stimulation system includes applying an electrical pulse during each of a set of successive oscillations in the measured electrophysiological signals, wherein the electrical pulse is applied at a stimulus phase at which the phase response curve has its substantially steepest positive slope.

6. The method of claim 1, wherein the phase response curve correlates phase of external stimulus delivery with phase of oscillation in the measured electrophysiological signals.

7. A method for controlling a closed-loop stimulation system having one or more electrodes configured to apply stimulating electrical signals and to receive electrophysiological signals, the method comprising:
   a. measuring, with the one or more electrodes of the closed-loop stimulation system, electrophysiological signals from a subject;

b. estimating a phase response curve from the measured electrophysiological signals;
c. computing a slope of the phase response curve;
d. determining electrical stimulation settings based on the computed slope of the phase response curve;
e. controlling the closed-loop stimulation system based on the determined electrical stimulation settings; and
f. applying a burst of electrical stimulation when the slope of the phase response curve is positive to decrease synchrony of a pathological oscillation in the subject.

8. The method of claim 7, wherein the system is a closed-loop deep brain stimulation system, and the electrophysiological activity signals are neural activity signals.

9. The method of claim 8, wherein controlling the stimulation system comprises applying an electrical stimulation to one or more neurons to suppress a pathological oscillation in the brain of the subject based on the slope of the phase response curve.

10. The method of claim 7, wherein controlling the closed-loop stimulation system includes applying an electrical pulse during each of a set of successive oscillations in the measured electrophysiological signals, wherein the electrical pulse is applied at a stimulus phase at which the phase response curve has its substantially steepest positive slope.

11. The method of claim 7, wherein the phase response curve correlates phase of external stimulus delivery with phase of oscillation in the measured electrophysiological signals.

12. A closed-loop stimulation system having:
a. one or more electrodes configured to apply stimulating electrical signals in the brain of a subject, and to receive electrophysiological signals in the brain of the subject; and
b. a controller configured to:
  i. measure electrophysiological signals received at the one or more electrodes;
  ii. estimate a phase response curve from the measured electrophysiological signals;
  iii. compute a slope of the phase response curve;
  iv. determine electrical stimulation settings based on the computed slope of the phase response curve; and
  v. apply electrical stimulation to one or more neurons to suppress a pathological oscillation in the brain of the subject based on the determined electrical stimulation settings using the one or more electrodes.

13. The system of claim 12, wherein the controller is configured to, when determining electrical stimulation settings, determine a phase window during which to apply a phasic burst stimulation, wherein the phase window is a range of phases during which the slope of the phase response curve has a positive slope.

14. The system of claim 12, wherein the controller is further configured to apply a phasic burst stimulation when the slope of the phase response curve is positive to decrease synchrony of oscillations in a subject.

15. The system of claim 12, wherein the controller is further configured to:
a. determine a phase window during which electrical stimulation is to be applied when determining electrical stimulation settings, wherein the phase window is a range of phases during which the slope of the phase response curve has a positive slope; and
b. apply a burst of electrical stimulation in the phase window.

16. A method for deep brain stimulation using a closed-loop deep brain stimulation system having one or more electrodes configured to apply stimulating electrical signals and to receive neural signals, the method comprising:
a. measuring neural signals from the brain of a subject using the one or more electrodes;
b. estimating a phase response curve from the measured neural signals;
c. computing a slope of the phase response curve;
d. determining electrical stimulation settings based on the computed slope of the phase response curve, wherein determining the electrical stimulation settings comprises determining a range of phases during which the slope of the phase response curve is positive; and
e. applying electrical stimulation based on the determined electrical stimulation settings using the one or more electrodes to suppress a pathological oscillation in the brain of the subject.

17. The method of claim 16 wherein the method further comprises applying a burst of electrical stimulation over substantially all of the range of phases.

18. The method of claim 16, further comprising decreasing synchrony of the pathological oscillation by applying a burst of electrical stimulation when the slope of the phase response curve is positive.

19. The method of claim 16, wherein controlling the closed-loop stimulation system includes applying an electrical pulse during each of a set of successive oscillations, wherein the electrical pulse is applied at a stimulus phase at which the phase response curve has its substantially steepest positive slope.

* * * * *

UNITED STATES PATENT AND TRADEMARK OFFICE
CERTIFICATE OF CORRECTION

PATENT NO. : 10,071,248 B2
APPLICATION NO. : 15/344723
DATED : September 11, 2018
INVENTOR(S) : Theoden Netoff et al.

It is certified that error appears in the above-identified patent and that said Letters Patent is hereby corrected as shown below:

In the Specification

Column 5, Line 65, Eq. (20, "$\delta_{i+1} = \varepsilon_i(1 + Z(\phi_i))$" should be -- $\varepsilon_{i+1} = \varepsilon_i(1 + Z'(\phi_i))$ --.

Signed and Sealed this
Sixth Day of November, 2018

Andrei Iancu
*Director of the United States Patent and Trademark Office*